(12) United States Patent
Rosenberg

(10) Patent No.: US 7,887,483 B2
(45) Date of Patent: Feb. 15, 2011

(54) SAFE MOUTH GAG

(75) Inventor: Lior Rosenberg, Omer (IL)

(73) Assignee: 4-MED Ltd., Kibbutz Nahal Oz (IL)

( * ) Notice: Subject to any disclaimer, the term of this patent is extended or adjusted under 35 U.S.C. 154(b) by 623 days.

(21) Appl. No.: 11/719,574

(22) PCT Filed: Nov. 17, 2005

(86) PCT No.: PCT/IL2005/001222

§ 371 (c)(1),
(2), (4) Date: May 17, 2007

(87) PCT Pub. No.: WO2006/054301

PCT Pub. Date: May 26, 2006

(65) Prior Publication Data

US 2008/0319270 A1    Dec. 25, 2008

(51) Int. Cl.
*A61B 1/32* (2006.01)
*A61B 1/24* (2006.01)
(52) U.S. Cl. .......... 600/238; 600/227; 600/228; 600/229; 600/223; 600/231; 600/232; 600/233; 600/224; 600/225; 600/245; 600/237; 600/239; 600/240; 600/241; 600/242; 600/243; 600/244
(58) Field of Classification Search .......... 600/209, 600/211, 102, 160, 227–245; 128/12, 13, 128/14, 15, 16, 17, 18, 19, 20, 341, 342, 128/345, 344; 606/239, 102, 160
See application file for complete search history.

(56) References Cited

U.S. PATENT DOCUMENTS 2,182,390 A * 12/1939 Reardon .............. 600/237
2,969,059 A     1/1961 Meek et al.
3,550,584 A    12/1970 Ring
4,024,859 A *  5/1977 Slepyan et al. .......... 600/215
4,151,837 A *  5/1979 Millard et al. ........... 600/215
4,213,451 A *  7/1980 Swenson ................. 600/215
5,897,491 A *  4/1999 Kastenbauer et al. .... 600/239
2005/0228232 A1* 10/2005 Gillinov et al. ......... 600/209

FOREIGN PATENT DOCUMENTS

GB        168 216        9/1921

* cited by examiner

Primary Examiner—Thomas C Barrett
Assistant Examiner—Sameh Boles
(74) Attorney, Agent, or Firm—AlphaPatent Associates Ltd.; Daniel J. Swirsky

(57) ABSTRACT

The present invention discloses a safe surgical mouth gag (MG) having a substantially planar frame larger than the maximal mouth aperture which is defined by at least two cross members, i.e., a longitudinal maxillary cross member and a mandibular cross member and by at least one rod connecting said maxillary and said mandibular cross members; and modules maneuverably interconnected to the same. The modules are selected from a tongue blade approximately perpendicular to the frames' plane, which is vertically displaceable with respect to said mandibular cross member; a retaining member within which said tongue blade shaft is slidably displaceable; retraction elements for urging the cheeks away from the oral cavity; abutment members for contacting the upper teeth or upper maxilla; and at least one light auxiliary located adjacent to oral cavity, adapted to illuminate the same effectively.

24 Claims, 22 Drawing Sheets

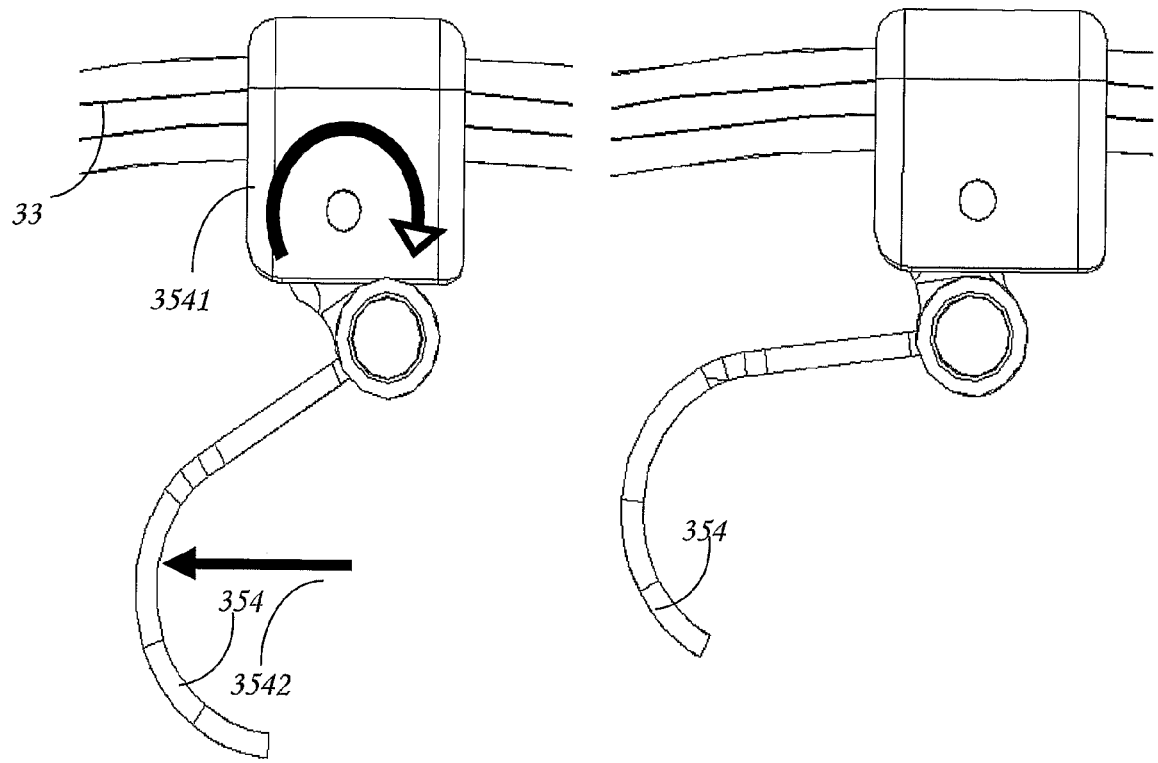
*Fig. 22A*      *Fig. 22C*
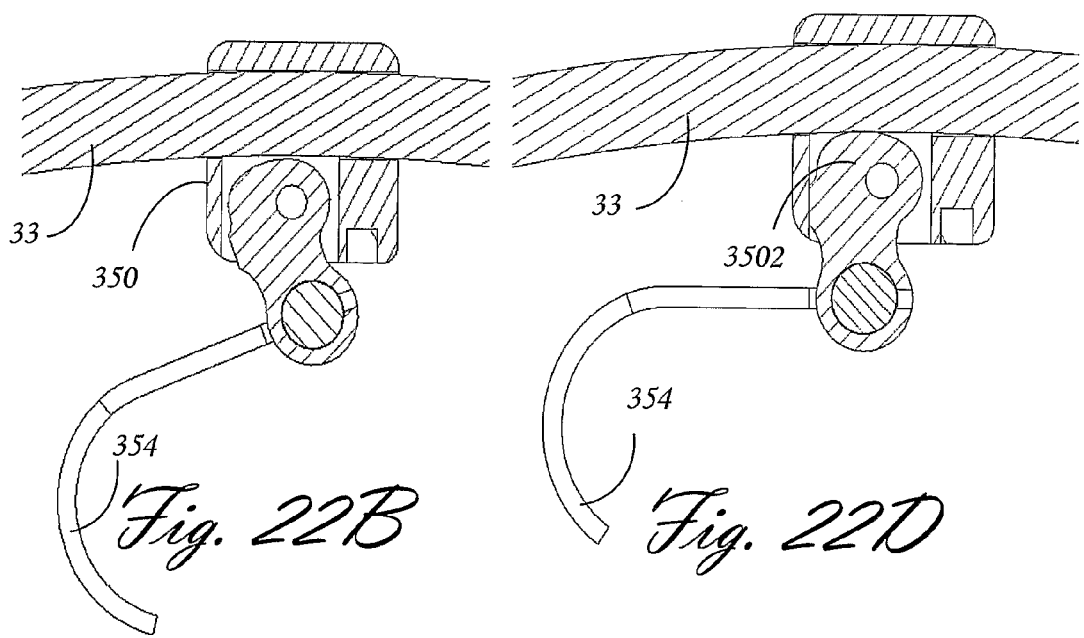
*Fig. 22B*      *Fig. 22D*

SAFE MOUTH GAG

FIELD OF THE INVENTION

The present invention generally relates to a safe surgical mouth gag and to a safe method utilizing the same.

CROSS-REFERENCE TO RELATED APPLICATIONS

This application is a U.S. National Phase Application under 35 U.S.C. 371 of PCT International Application No. PCT/IL2005/001222, which has an international filing date of Nov. 17, 2005, and which claims priority from Israel Patent Application No. IL165301, filed Nov. 18, 2004, both of which are incorporated herein by reference in their entirety.

BACKGROUND OF THE INVENTION

A surgical mouth gag (MG) is a retraction device which is insertable into the oral cavity, and is used for surgical procedures of the oral cavity and upper larynges/pharynges in order to provide added accessibility thereto and to keep the mouth open as widely as possible, while retracting the tongue and cheeks from the operation field. MG must be capable of being safely and simply inserted into, and removed from, the oral cavity, a feature which has particular utility during emergency conditions; It provides free access to the operation field by safely and effectively retracting away all the oral cavity's structures such as tongue, maxilla, mandible and cheeks; It is configured to protect, without interference with artificial ventilation airway-devices, such as intra-tracheal tubes or laryngeal masks; Its components do not obstruct the vision of a surgeon and do not interfere in any way with surgical procedures in the oral cavity associated with instruments, devices or systems needed for such surgical procedures; and, it provides illumination for the dark recesses of the surgical field.

Prior art mouth gags comprise means for keeping the jaws ajar and for pressing the tongue away from the oral cavity, and some also comprise lateral retraction arms that retract lateral mouth commissures and cheeks from the oral cavity.

A prior art MG, which is commonly referred to as a Dingman mouth gag and which has been widely used by surgeons for over 70 years, is illustrated in FIG. 1. This prior art MG, which is generally designated by numeral 10, comprises substantially planar frame 5 larger than the maximal mouth aperture, lateral retraction arms 7 which pivot and rotate about a corresponding side rod 9 of the frame, for urging the cheeks away from the oral cavity, laterally displaceable along the frame's upper arm and secured by locking joint 23 teeth blades 11 for contacting the upper teeth or maxilla, and tongue blade 15 and tongue blade shaft 16, the latter being slidable in holder 18 so that tongue blade 15 may be displaced with respect to lower portion 4 of the frame. Latch 21 is used to secure shaft 16 to holder 18 and key 23 is used to set the angular position of a retraction arm 7 to the corresponding side rod 9. Tongue blade 15 is fitted over a ventilation tube (not shown), which is introducible to the trachea of a patient, by means of open region 14 formed in tongue blade 14, such that the latter overlies, and is contact with the ventilation tube.

The Dingman mouth gag, which is the most advanced of all prior art mouth gags and which allows retraction to all directions, suffers from the following drawbacks:

Engagement: Considerable dexterity and skill in manipulating the MG are needed in order to introduce it into the mouth, engage the lower jaw and the tongue without moving the ventilation tube, to engage the upper jaw, retain and retract the jaws to an open position, and to urge the tongue and cheeks away from the oral cavity, particularly since the tongue blade 15 and retraction arms 7 freely move in different directions when released. All these operations should be executed without moving the centrally positioned ventilation tube and without pinching soft tissues such as the tongue and lips. At times, due to the difficulty in manipulating the various components of the MG, misalignment results. Consequently, for example, the tongue blade loses contact with the tongue, parts of the tongue protrude between the tongue blade and the lower mandible alveoli, the ventilation tube can be displaced or pinched and occluded, the teeth blades need to be repositioned, and the MG needed to be urgently removed from the oral cavity and reinserted therein after proper ventilation has been established.

Removal: The removal of the MG from the oral cavity is potentially hazardous as the entire structure with all its retracting arms should be pulled out as one and the ventilation tube is liable to become imbedded in swollen oral tissue or adhere to the tongue blade by desiccated secretions or coagulated blood and be accidentally removed together with the MG.

During a removal procedure, the ventilation tube is liable to be displaced, thereby endangering the life of the patient. At times, an emergency removal procedure is needed, such as a result of an anesthesia-related complication, and difficulty in manipulating the MG is liable to lead to additional medical problems, and even to death. For example, a relatively high moment needs to be applied to key 23 of retraction arm 23, from the inner cheek. The cumbersome removal procedure generally requires several minutes.

Individual anatomical variations: Due to individual anatomical variations, the MG components need to be individually set and adjusted for each patient and the existing devices and their parts are difficult or in some cases impossible to manipulate.

The lower jaw/tongue complex: In order to accommodate the anatomical variations associated with the relative dimensions of the lower jaw and tongue, a stock of tongue blades, e.g. 3-6, each of which has a different length and width, is needed. A selected tongue blade is adapted to contact the tongue, so as to be retracted from the oral cavity and to be retained within the alveolar arch of the lower jaw. However, a selected tongue blade may not necessarily cover the entire tongue, and regions of the tongue protruding from the tongue blade tend to swell, remaining in the oral cavity and interfering with the surgical field. Due to this interference, the MG is liable to move, requiring readjustment of the various components thereof.

Tube protection: The tongue blade is liable to compress and obstruct the ventilation tube, particularly in the vicinity of the teeth. Body heat warms the tube, which consequently becomes soft and susceptible to collapse, bending and obstruction, often leading to disruption in the passage of air therethrough.

Ergonomics: Manipulation of the MG is cumbersome. The use of surgical instruments is additionally problematic, due to the configuration of components such as angles, protrusion, latch 21 and key 23 protruding from frame 5, resulting in the entanglement of suturing threads.

Illumination: An external upper surgical lamp and/or headlight are generally required. These types of illumination cast their light downward into the bottom of the oral cavity (posterior wall), and are difficult to control and direct into many of the dark upper and lateral oral recesses. Furthermore, shadows are cast from the surgical instruments and from the hands of the surgeon.

U.S. Pat. No. 4,024,859 discloses a mouth gag wherein the entire side member of the frame rotates, allowing a faster (but not safer) release and insertion, but otherwise suffers from all of the aforementioned drawbacks.

It is an object of the present invention to provide a surgical mouth gag which is easily and safely applied into and removable from, the oral cavity.

It is an object of the present invention to provide a surgical mouth gag which reduces the risk of potentially hazardous ventilation tube kink or displacement.

It is an additional object of the present invention to provide a surgical mouth gag to which the tongue blade may be set in an ergonomic position for introduction, use and removal.

It is a further object of the present invention to provide a surgical mouth gag in which all the retracting blades and their release is done in an ergonomic way.

It is yet another object of the present invention to provide a surgical mouth gag which prevents protrusion of the tongue around the tongue blade.

It is an additional object of the present invention to provide a surgical mouth gag which is configured such that suturing thread entanglement is precluded.

It is still another object of the present invention to provide a surgical mouth gag that will allow a good illumination to reach all oral recesses It is yet an additional object of the present invention to provide a surgical mouth gag which overcomes the drawbacks of the prior art.

Other objects and advantages of the invention will become apparent as the description proceeds.

SUMMARY OF THE INVENTION

It is thus one object of the present invention to present a safe surgical mouth gag (MG) comprising a substantially planar frame larger than the maximal mouth aperture which is defined by at least two cross members, i.e., a longitudinal maxillary cross member and a mandibular cross member and by at least one rod connecting said maxillary and said mandibular cross members; and modules maneuverably interconnected to the same. Said modules are selected from a tongue blade having an elongated shaft approximately perpendicular to said frames' plane, which is vertically displaceable with respect to said mandibular cross member; a retaining member within which said tongue blade shaft is slidably displaceable, adapted for reversibly retaining said tongue blade at a predetermined vertical distance with respect to said mandibular cross member; said mandibular cross member and the entire frame is rotatable with respect to said retaining member; retraction elements for urging the cheeks away from the oral cavity; the said are pivotally maneuverable about said maxillary cross member and are laterally displaceable; abutment members for contacting the upper teeth or upper maxilla, pivotally maneuverable about said maxillary cross member and are laterally displaceable; and at least one light auxiliary located adjacent to oral cavity, adapted to illuminate the same effectively. A prompt removal of the aforesaid MG from the oral cavity is ensured, also in an emergency removal procedures, individually set and adjusted for each patient and the existing devices and their parts are difficult or in some cases impossible to manipulate.

Another object of the present invention is to disclose the said MG wherein the retaining member comprises an inwardly facing track within which the tongue blade shaft is slidably displaceable; an outwardly facing concave seat for receiving each corresponding elliptical element; a locking assembly for preventing the rotation of the maxillary cross member; and means for setting the vertical distance between the tongue blade and the mandibular cross member.

Another object of the present invention is to disclose the said MG wherein the track has two opposed vertically extending buccal faces which are formed with upper and lower stepped portions at the inner edge thereof, guide elements laterally extending from the inner edge of said upper and lower stepped portions defining the track within which the shaft is slidable.

Another object of the present invention is to disclose the said MG wherein the locking assembly is provided with a button having a pointed upper portion and a helical spring which biases the button upwardly.

Another object of the present invention is to disclose the said MG wherein the retaining element is adapted to rotate 90 degree around the maxillary cross member and further adapted to be locked into either positions.

Another object of the present invention is to disclose the said MG wherein the mandibular cross member is provided with two equally sized planar elements which are recessed at diametrically opposite ends thereof, the pointed upper portion of the locking assembly button being in a pressing relation with one of said planar elements when the button is raised.

Another object of the present invention is to disclose the said MG wherein the maxillary cross member is prevented from rotating in one rotational direction due to the force applied by the pointed upper portion of the locking assembly button onto the corresponding planar element and is prevented from rotating in the other rotational direction due to the reactive force applied by a seat onto the corresponding elliptical element.

Another object of the present invention is to disclose the said MG wherein the tongue blade comprises a fixed section connected to the shaft and essentially perpendicular thereto, and two horizontally displaceable elements underlying or overlying said fixed section, by which the width of the tongue blade is adjustable.

Another object of the present invention is to disclose the said MG wherein the tongue blade is provided with an opening through which an endotracheal tube is insertable.

Another object of the present invention is to disclose the said MG wherein the button, angles protrusions and setting means are curvilinear.

Another object of the present invention is to disclose the said MG wherein the retaining member is detachable from the maxillary cross member.

Another object of the present invention is to disclose the said MG wherein the retraction element comprises a carrier which is laterally displaceable along, and rotatable about, the maxillary cross member; an arm pivotally connected to said carrier by means of a pin fixedly mounted onto opposed side faces of said carrier; a release trigger for said arm; and a U-shaped retractor blade connected to said arm such that a curved portion of said blade is lingually oriented.

Another object of the present invention is to disclose the said MG wherein the arm has a curvilinear head portion configured such that the rotation of the retraction element about the maxillary cross member is prevented when said head portion is in pressing engagement with the maxillary cross member.

Another object of the present invention is to disclose the said MG wherein the retraction element is provided with means for preventing the lateral displacement thereof.

Another object of the present invention is to disclose the said MG wherein each abutment member is laterally displaceable along, and rotatable about, the maxillary cross member.

Another object of the present invention is to disclose the said MG wherein the abutment member comprises a hollow partial cylindrical wall; substantially straight elongated walls extending from each end of said cylindrical wall and joining at a common distal end;, a protrusion extending into the interior of said cylindrical wall for engaging a similarly shaped laterally extending groove formed in the maxillary cross member; and a plurality of mutually parallel lips formed in the exterior of one of said elongated walls for abutting a suitable area within the oral cavity and for subsequently prying the jaws to a maximal opening.

Another object of the present invention is to disclose the said MG wherein the abutment member is rotatable about the maxillary cross member upon disengagement of the protrusion from the similarly shaped groove.

Another object of the present invention is to disclose the said MG which further comprises a light source which is releasably attachable to the frame and directable to any desired region of the oral cavity without casting a shadow.

Another object of the present invention is to disclose the said MG which further comprises a guard for an endo-tracheal tube.

Another object of the present invention is to disclose the said MG wherein the tube guard is U-shaped.

Another object of the present invention is to disclose the said MG wherein the tube guard is connected to the fixed section of the tongue blade.

Another object of the present invention is to disclose the said MG wherein the tube guard is horizontally displaceable.

Another object of the present invention is to disclose the said MG wherein the inclination of the tube guard is adjustable.

Another object of the present invention is to disclose the said MG wherein the tube guard is in the form of one or two spacer-blocks between the tongue blade and the teeth.

Another object of the present invention is to disclose the said MG which is quickly collapsible.

A safe method for engaging a surgical mouth gag within the oral cavity is hereto disclosed. This method comprises steps selected from providing a substantially planar frame larger than the maximal mouth aperture which is defined by a longitudinal first mandibular cross member and second maxillary cross member and by two side rods connecting said first and maxillary cross members; retraction elements for urging the cheeks away from the oral cavity, which are pivotable about said maxillary cross member and are laterally displaceable; abutment members for contacting the upper teeth or upper maxilla; a tongue blade having an elongated shaft essentially perpendicular thereto, which is vertically displaceable with respect to said maxillary cross member; and a retaining member, within which said tongue blade shaft is slidably displaceable, which is adapted for retaining said tongue blade at a predetermined vertical distance with respect to said maxillary cross member, and with respect to which the maxillary cross member and the frame is rotatable; rotating the frame approximately 90 degrees with respect to said tongue blade; upwardly rotating said retraction elements above said maxillary cross member; orienting said abutment members such that a distal end thereof is vertically above said cross member; raising said tongue blade to its uppermost position; introducing said tongue blade into the oral cavity by a procedure similar to the insertion of a laryngoscope into the oral cavity; adjusting the two tongue blade's "wings" to cover the entire tongue in its mandibular bed; placing the endotracheal tube into the depression or introducing it through an opening formed within the tongue blade; rotating the frame approximately 90 degrees until the side rods thereof are essentially vertically disposed; lowering the frame onto the oral cavity; rotating said abutment members against the maxillary teeth or alveoli; retracting said tongue blade until the tongue and the mandible is retracted opening the oral cavity; rotating said retraction elements into the oral cavity; and buccally displacing said retraction elements to a maximal extent until an arm of each of said retraction elements is in pressing engagement with said maxillary cross member.

BRIEF DESCRIPTION OF THE FIGURES

In order to understand the invention and to see how it may be implemented in practice, a plurality of embodiments will now be described, by way of non-limiting example only, with reference to the accompanying drawings, in which.

DETAILED DESCRIPTION OF THE PREFERRED EMBODIMENTS

The following description is provided, alongside all chapters of the present invention, so as to enable any person skilled in the art to make use of said invention and sets forth the best modes contemplated by the inventor of carrying out this invention. Various modifications, however, will remain apparent to those skilled in the art, since the generic principles of the present invention have been defined specifically to provide a safe surgical mouth gag (MG) and a safe method utilizing the same.

Figure 1:
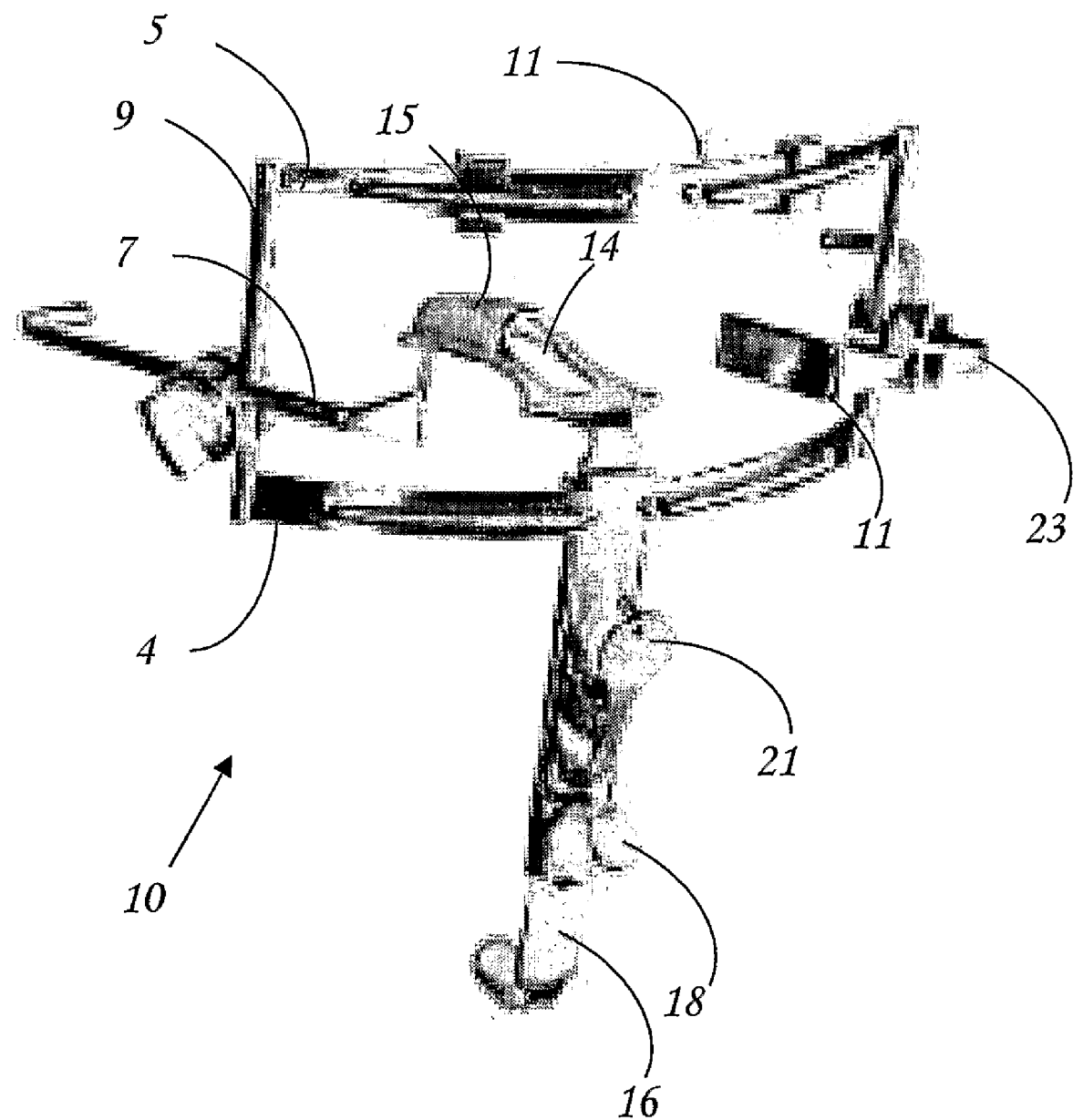
FIG. 1 is a perspective view of a prior art mouth gag.

The present invention is a safe surgical mouth gag (MG) provided with a tongue blade which is angularly pivotable with respect to the MG frame. Accordingly, the frame of the MG can be applied above the mouth following the positioning of tongue blade into the oral cavity (similar to a laryngoscope), thereby reducing the risk of ventilation tube displacement existing with respect to prior art mouth gags, which would be fatally dangerous to an anesthetized and intubated patient. While the manipulation of a Dingman prior art mouth gag (10) illustrated in FIG. 1 is cumbersome due to the freely moving components and fixed position thereof, the components of the MG of the present invention are self-locking and easily releasable, thereby facilitating quick and simple insertion and removal of the MG, without risk of endangering the patient.

The present invention provides a surgical mouth gag, comprising a frame consisting of two laterally extending cross members and two side rods, and oral cavity retraction and/or positioning elements, for urging oral cavity parts away from their normal position or for keeping oral cavity parts in a predetermined fixed position, characterized in that said retraction and/or positioning elements are displaceable along, or rotatable around, or pivotally connected to, said frame. The oral cavity parts are selected from the cheeks, teeth, upper and lower maxilla or tongue.

In one embodiment of the invention, the surgical mouth gag comprises a substantially planar frame larger than the maximal mouth aperture which is defined by a longitudinal maxillary cross member ("mandibular") and maxillary cross member ("maxillar") and by two side rods connecting said first and maxillary cross members; retraction elements for urging the cheeks away from the oral cavity, which are pivotable about said maxillar cross member and are longitudinally displaceable; abutment teeth-blade members for contacting the upper teeth or upper maxilla; a tongue blade having an elongated shaft essentially perpendicular thereto, which is vertically displaceable with respect to said first, mandibular cross member; and a retaining member, within which said tongue blade shaft is slidably displaceable and which is adapted for retaining said tongue blade at a predetermined vertical distance with respect to said maxillary cross member, wherein said maxillary cross member is rotatable with respect to said retaining member.

As referred to herein, "vertical" is in a direction similar to, but not identical to the disposition of the teeth, one vertical direction being defined as "upper" or "above", i.e. towards the maxillary upper jaw, and the opposite vertical direction being defined as "lower" or "downwardly", i.e. mandibular towards the lower jaw. "Lateral" is in a direction corresponding to the width of the oral cavity, one lateral direction being defined as a "buccal" direction, i.e. towards the cheeks, and the opposite longitudinal direction being defined as a "lingual" direction, i.e. towards the tongue. "Inwards" or "inner" is in a direction towards the oral cavity. "Outwards" or "outer" is in a direction away from the oral cavity. Although these directions are defined when the mouth gag is engaged within the oral cavity, they may also be used to describe the configuration of the various components thereof when the mouth gag is removed from the oral cavity.

In an embodiment of the invention, the retaining member is pivotally connected to one or more elliptical elements, each elliptical element being fixedly mounted onto the maxillary cross member. The retaining member comprises an inwardly facing track within which the tongue blade shaft is slidably displaceable; an outwardly facing concave seat for receiving each corresponding elliptical element; a locking assembly for preventing the rotation of the maxillary cross member; and means for setting the vertical distance between the tongue blade and the maxillary cross member.

In yet another embodiment of the invention, the aforesaid track has two opposed vertically extending buccal faces which are formed with upper and lower stepped portions at the inner edge thereof. Guide elements are laterally extending from the inner edge of said upper and lower stepped portions thus defining said track within so as the shaft is slidable;

According to another embodiment of the invention, the locking assembly is provided with a press-button having a pointed upper portion and a spring which biases the button upwardly.

According to another embodiment of the invention, the maxillary cross member is provided with two equally sized planar members that are recessed at diametrically opposite ends thereof. The pointed upper portion of the locking assembly button is being in a pressing relation with one of said planar elements when the said button is raised.

According to another embodiment of the invention, the rotation of said maxillary cross member is prevented in one rotational direction by applying a suitable force by means of the pointed upper portion of the locking assembly button, onto the corresponding planar member. Its rotation to the opposite direction is prevented by a reactive force applied by a seat onto the corresponding elliptical element.

According to another embodiment of the invention, the tongue blade comprises at least one fixed section connected to the shaft and essentially approximately perpendicular thereto, and two horizontally displaceable elements, hereinafter being referred in the term 'wings', underlying said fixed section, by which the width of the tongue blade is adjustable.

According to another embodiment of the invention, the aforesaid tongue blade is provided with an aperture through which an endotracheal tube is insertable and a depression that can accommodate said endotracheal tube.

According to another embodiment of the invention the button and setting means are curvilinear.

According to another embodiment of the invention the retaining member is detachable from the maxillary cross member.

In one possible aspect of the present invention, the retraction element comprises a carrier which is laterally displaceable along, and rotatable about the maxillary cross member; an arm pivotally connected to said carrier by means of a pin fixedly mounted onto opposed side faces of said carrier; a release trigger for said arm; and a U-shaped retractor blade connected to said arm such that a curved portion of said blade is lingually oriented.

According to another embodiment of the invention, the arm comprises a curvilinear head portion, configured such that the rotation of the retraction element about the maxillary cross member is prevented when said head portion is in pressing engagement with the maxillary cross member.

According to another embodiment of the invention the retraction element is preferably provided with means for preventing the lateral displacement thereof.

According to another embodiment of the invention, each abutment member is laterally displaceable along, and rotatable about, the maxillary cross member.

According to another embodiment of the invention, the abutment member comprises a hollow partial cylindrical wall; substantially straight elongated walls extending from each end of said cylindrical wall and joining at a common distal end;, a protrusion extending into the interior of said cylindrical wall for engaging a similarly shaped laterally extending groove formed in the maxillary cross member; and a plurality of mutually parallel lips formed in the exterior of one of said elongated walls for abutting a suitable area within the oral cavity and for subsequently prying the jaws to a maximal opening.

According to another embodiment of the invention, the abutment member is rotatable about the said maxillary cross member upon disengagement of the protrusion from the similarly shaped groove.

According to another embodiment of the invention, the surgical mouth gag further comprises a guard for an endrotracheal tube. The tube guard may be U-shaped, connected to the fixed section of the tongue blade, horizontally displaceable, or having an inclination which is adjustable. Preferably, the surgical mouth gag is quickly collapsible.

Figure 2:
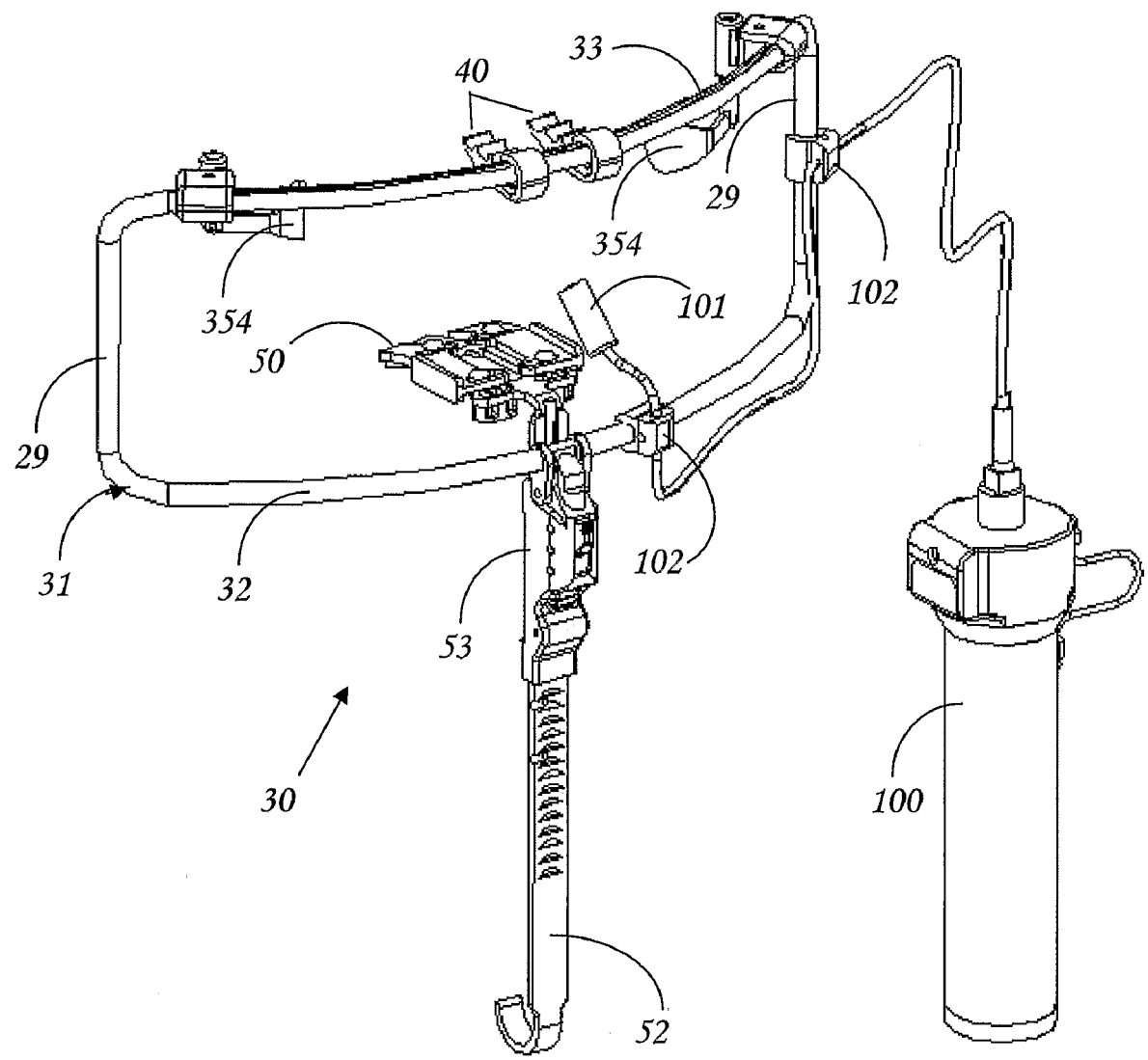
FIG. 2 is a perspective view of a mouth gag, according to one embodiment of the present invention.

Reference is made now to FIG. 2, which illustrates one embodiment of the mouth gag according to the present invention, and is generally indicated by numeral 30. MG 30 comprises substantially planar frame 31 larger than the maximal mouth aperture, which is defined by lateral two side rods 29 connecting mandibular cross member 32 and maxillary cross member 33, longer than the mouth width, retraction elements 35 for urging the cheeks laterally away from the oral cavity, which are pivotable about maxillary cross member 33 and are laterally displaceable, maxillary teeth abutment members 40 for contacting the upper teeth or upper maxilla which are pivotable about maxillary cross member 33 and are laterally displaceable, tongue blade 50 having an adjustable width and an elongated shaft 52 being essentially perpendicular thereto, which is vertically pivotable with respect to mandibular cross member 32, and retaining member 53, within which tongue blade shaft 52 is slidably displaceable and which is adapted for retaining tongue blade 50 at a predetermined distance with respect to mandibular cross member 32. Light is possibly emitted by at least one light source 101 maneuverably mounted on frame 31, e.g., on mandibular cross member 32, by means of clip 102. Said light source 101 is possibly in communication with an electrical source 100.

Figure 3:
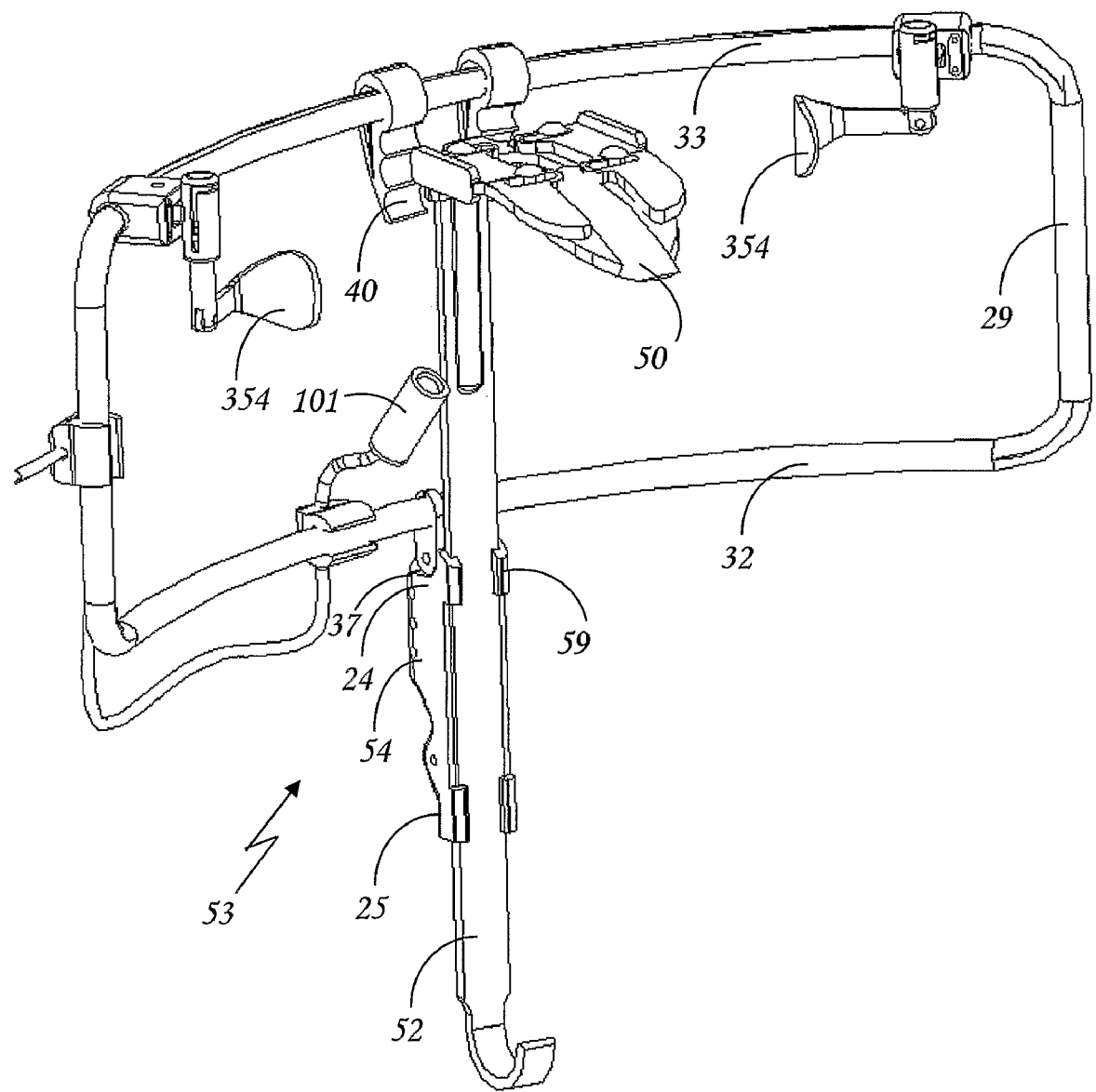
FIG. 3 is a perspective view of a mouth gag, according to yet another embodiment of the present invention.
Figure 4:
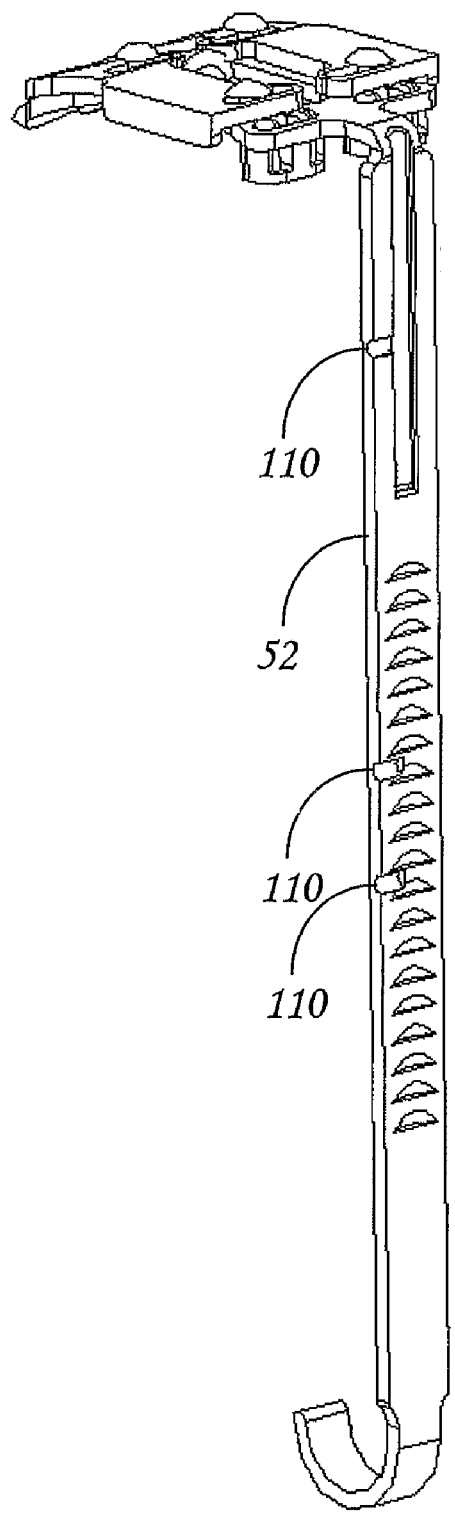
FIG. 4 is a perspective view of the tongue blade.

FIG. 3 discloses a device according to yet embodiment of the present invention, wherein retaining member 53 has two opposed vertically extending buccal faces 54. A guide element 59 laterally extends from the inner edge of an upper stepped portion 24 and lower stepped portion 25 of each corresponding buccal face 54 of the retaining member. Guide elements 59 define a track within which shaft 52 is slidable. FIG. 4 presents tongue blade shaft 52, which comprises a plurality of recesses 110 adapted to avoid said shaft of accidental sliding downwardly.

Figure 5:
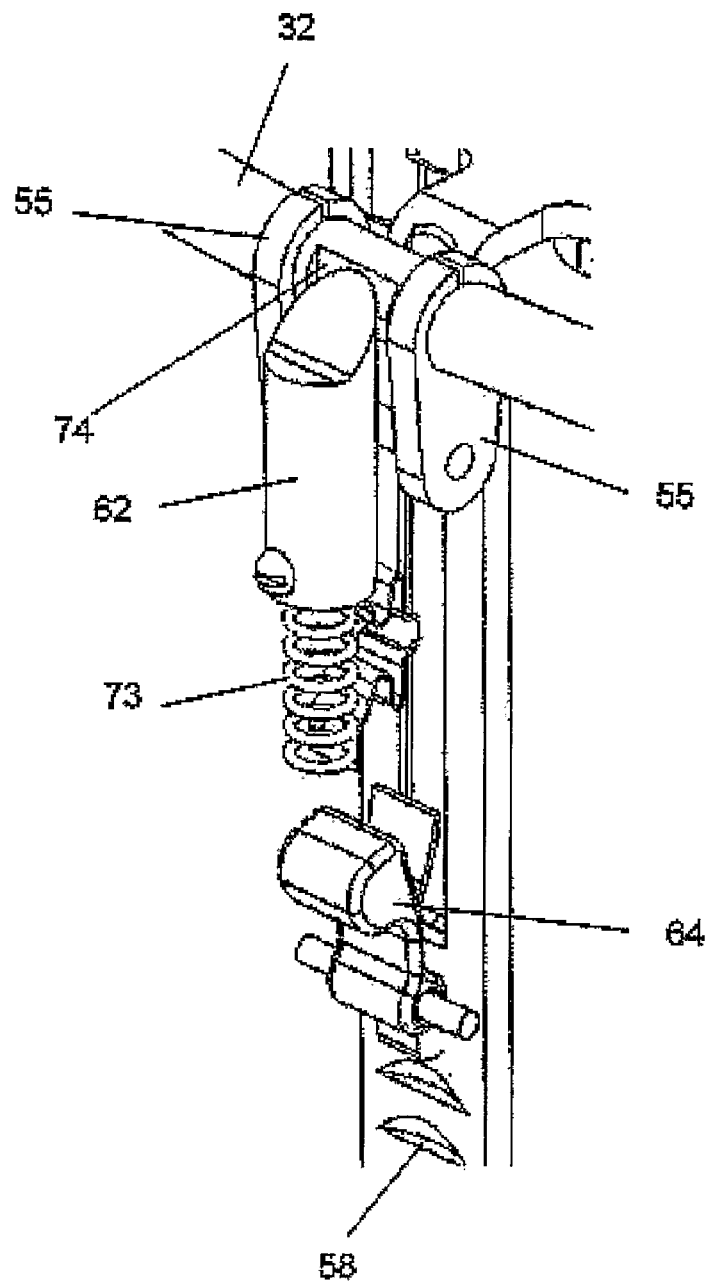
FIG. 5 is a perspective view of the retaining member, with the locking assembly housing being removed.
Figure 6:
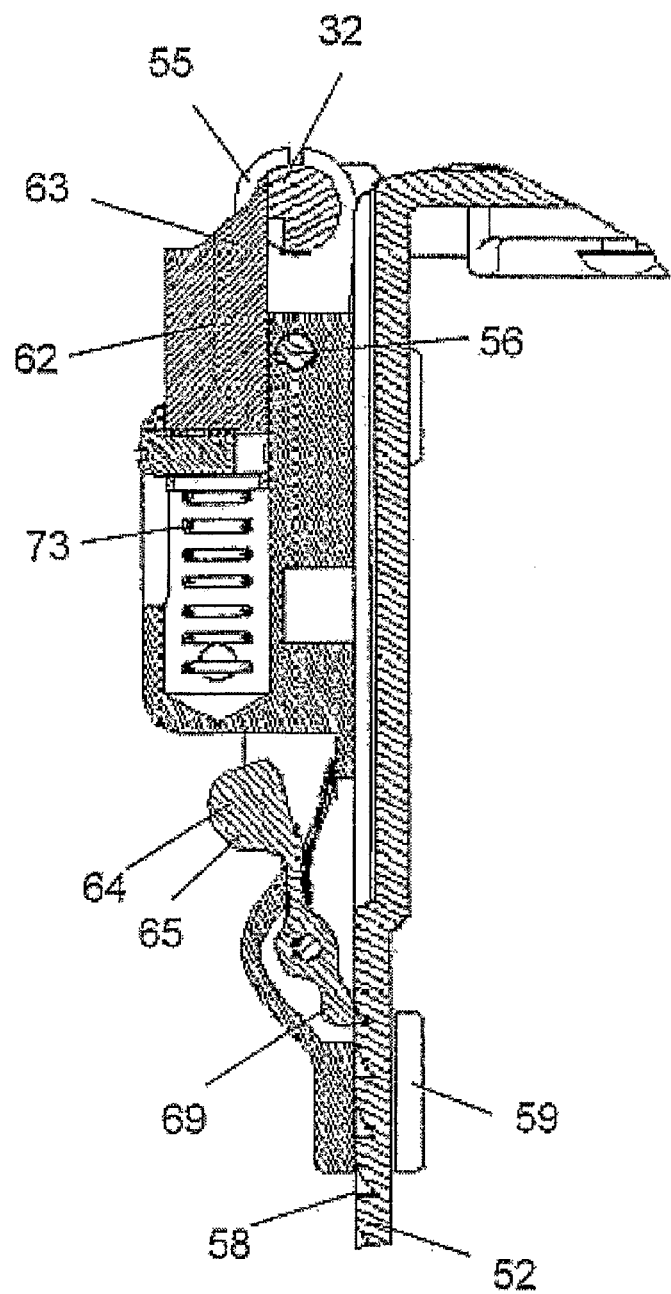
FIGS. 6 and 7 are enlarged elevational cross sectional views of the retaining member, showing an elliptical element carried by a maxillary cross member of the mouth gag frame as the frame is in vertical and horizontal dispositions, respectively.

Referring to FIGS. 5 and 6, the distance between tongue blade 50 (FIG. 4) and first mandibular cross member 32 is set, according to the particular preferred embodiment of this figure, by means of ratchet 64, which engages a selected recess 58 formed in the outer face of tongue blade shaft 52. Ratchet 64 is preferably made of a pliable material (but can be of any other type) and comprises an accurate upper portion 65, a pointed or of any other suitably shaped lower portion 69 which engages a similarly shaped recess 58. The operation of the ratchet is well understood by the skilled person and, therefore, it will not be explained in greater detail, for the sake of brevity.

As shown in FIGS. 3 and 6, retaining member 53 is pivotally connected by means of two pin joints 56 to corresponding elliptical elements 55, which in turn are fixedly mounted onto maxillary cross member 32. Consequently, maxillary cross member 32 is rotatable with respect to retaining member 53 and to tongue blade 50.

The angular disposition of the MG frame with respect to the retaining member is fixed by means of locking assembly, as shown in FIGS. 3, 5, 6 and 7. Locking assembly is provided with button 62 having a cylindrical lower portion and a pointed upper portion 63, and helical spring 73 which biases the button upwardly. When button 62 of the locking assembly is in a raised position, pointed upper portion 63 is in a pressing relation with recessed portion 74 of the maxillary cross member 32, which is interposed between the two elliptical elements 55. The locking assembly is depressed by the maxillary cross member when the latter is rotated and locks in place. As shown, recessed portion 74 is defined by two equally sized planar, rectangular elements which are recessed at diametrically opposite ends of the tubular maxillary cross member 32. With respect to the orientation shown in FIG. 3, maxillary cross member 32 is prevented from rotating in a counterclockwise direction due to the force applied by pointed upper portion 63 onto recessed portion 74. Maxillary cross member 32 is prevented from rotating in a clockwise direction due to the reactive force provided by seat 37 onto the adjacent long side of elliptical element 55, which is vertically disposed.

Figure 7:
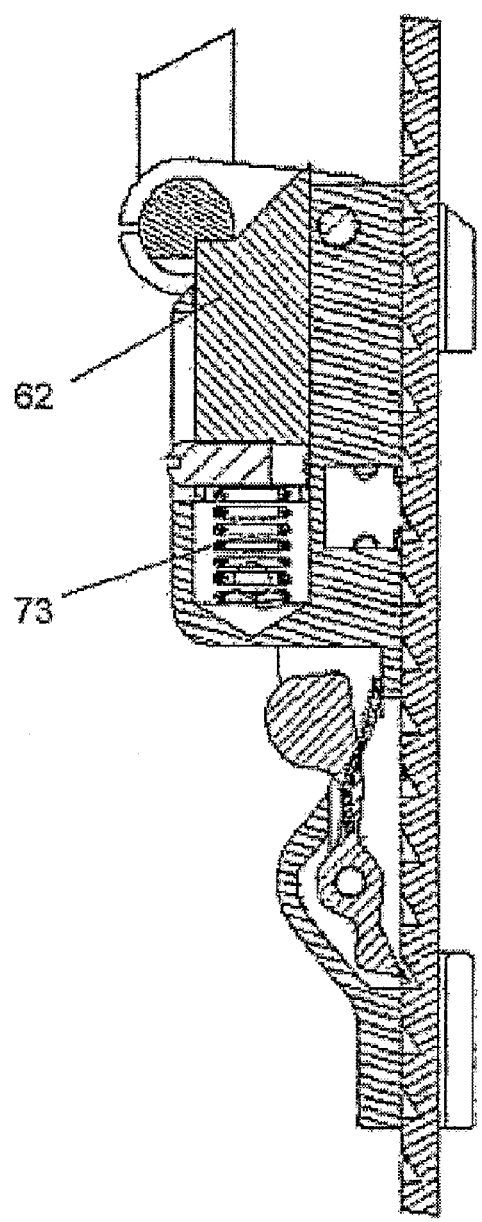

When button 62 is depressed, as shown in FIG. 7, the pointed upper portion ceases to bear on the recessed portion of the maxillary cross member.

Figure 8:
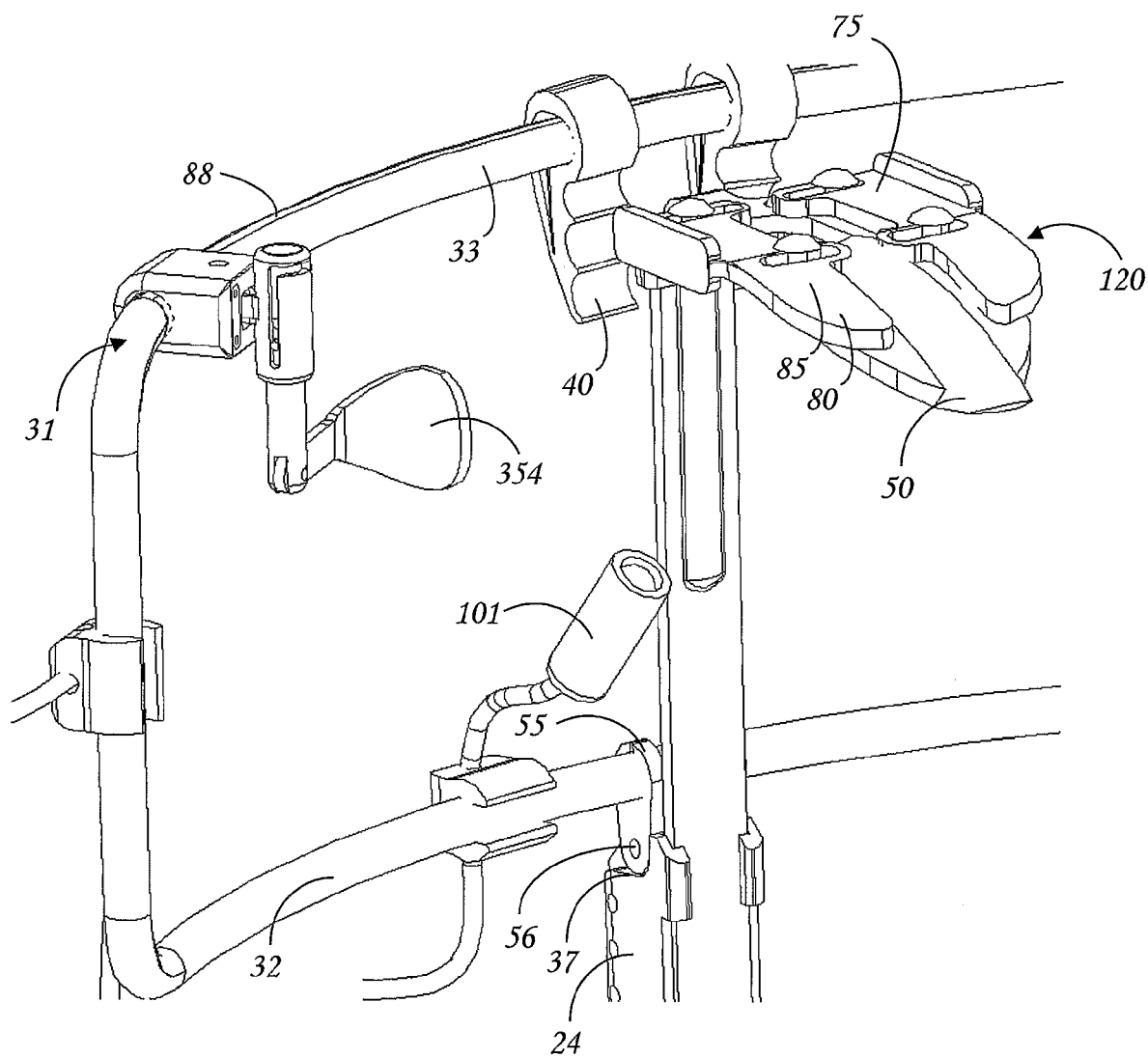
FIGS. 8-11 are perspective close views of the mouth gag of FIG. 2.
Figure 9:
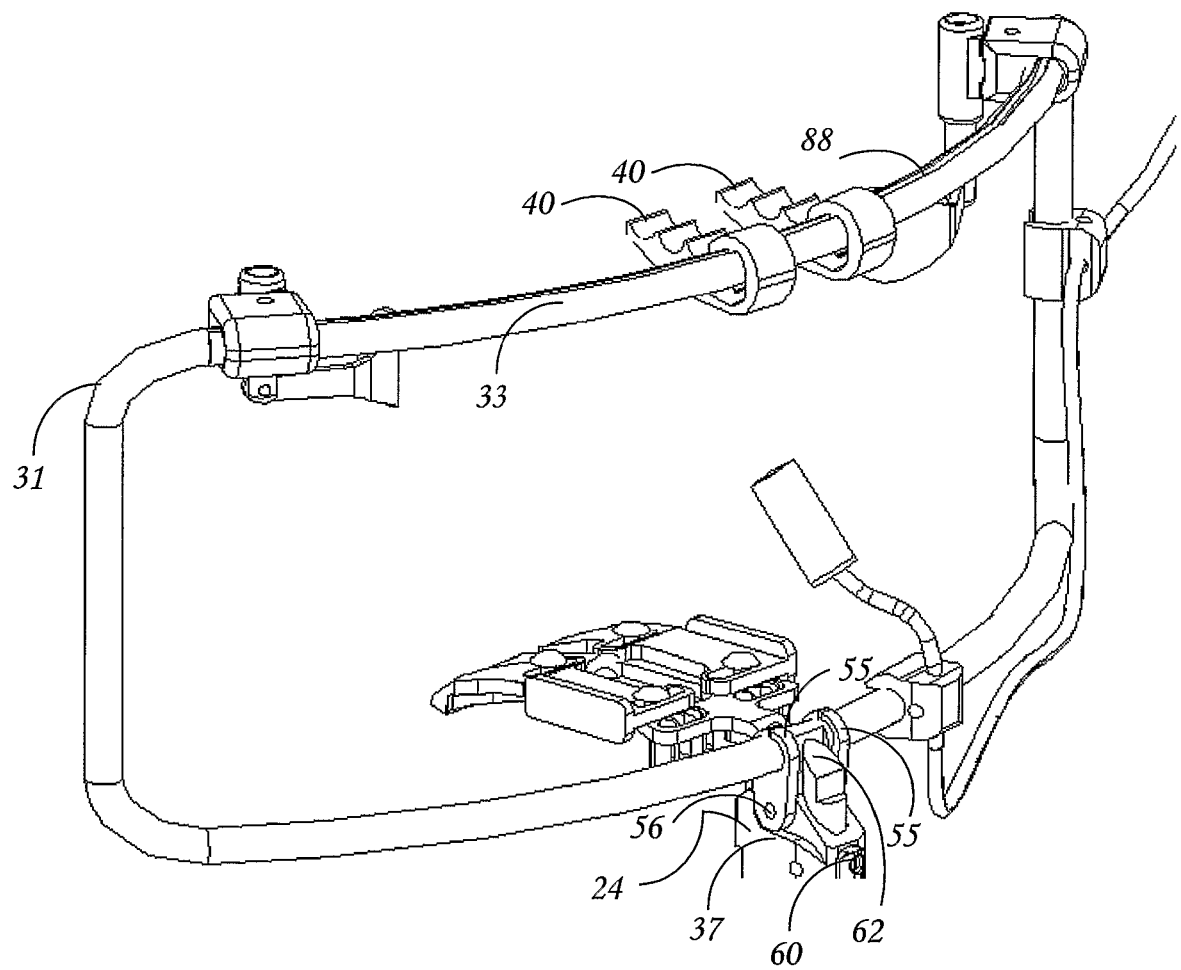
Figure 10:
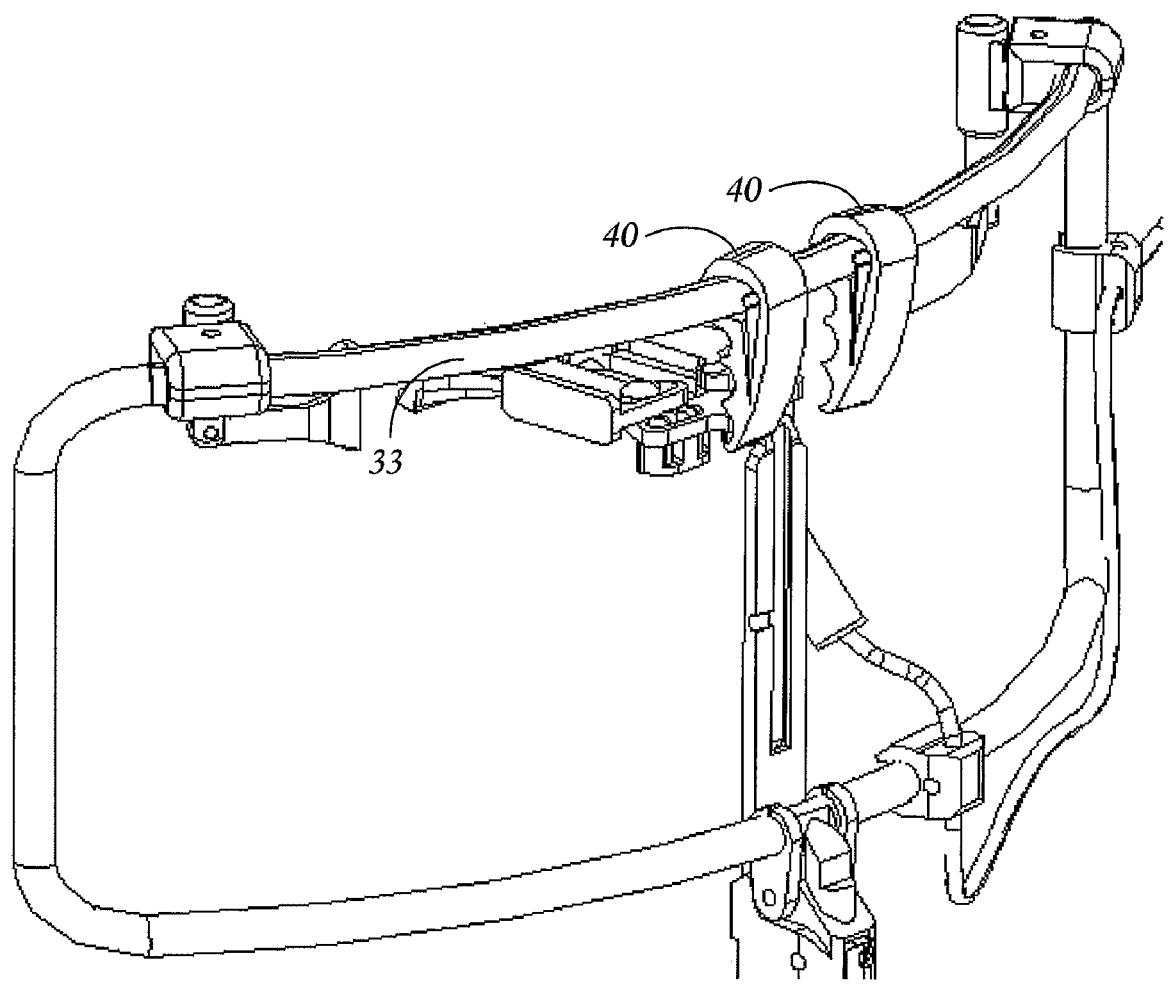
Figure 11:
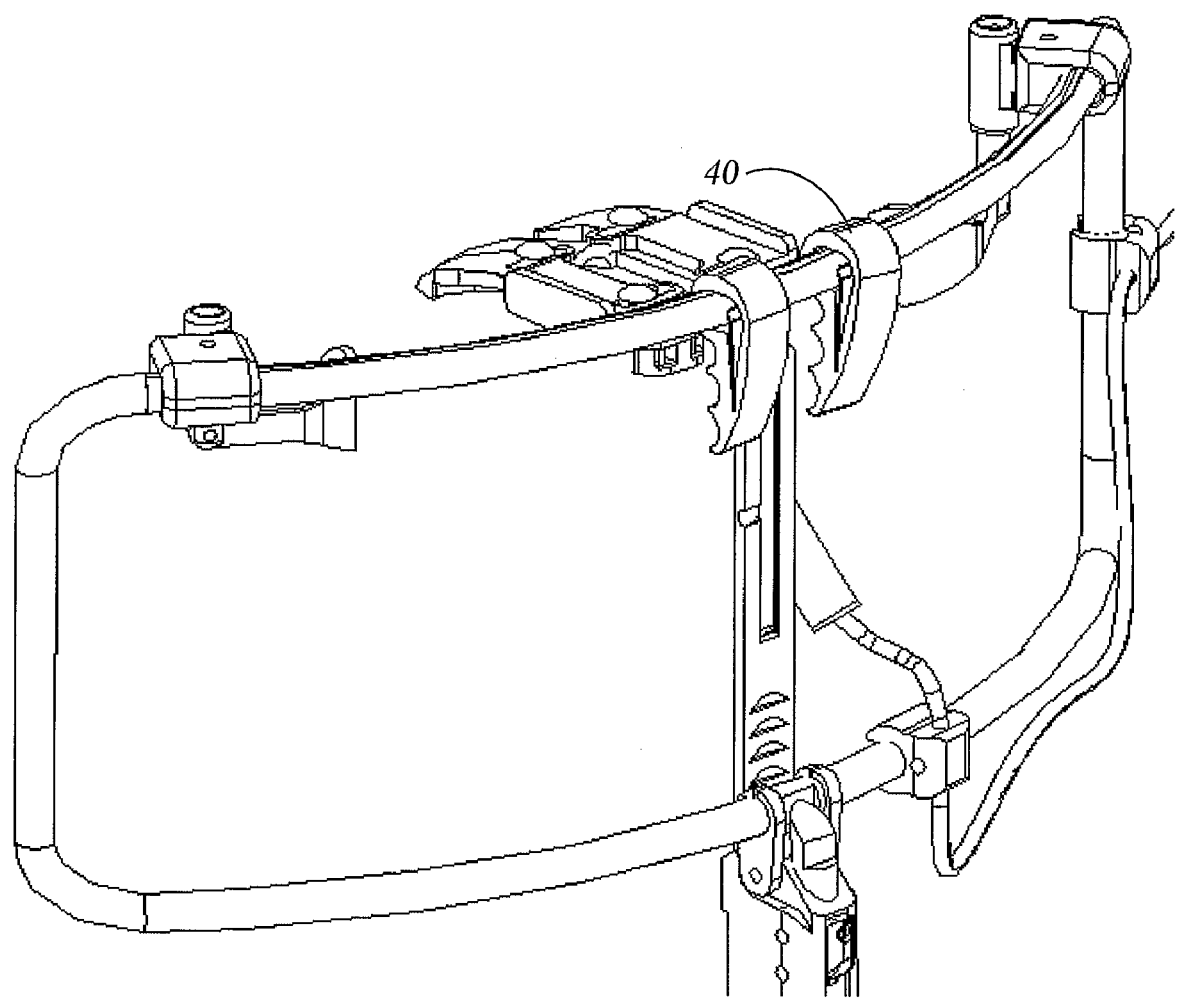

With respect to the orientation shown in FIG. 8, maxillary cross member 32 is then free to rotate in a counterclockwise direction. Each elliptical element 55, which is fixedly mounted onto the maxillary cross member, likewise rotates in a counterclockwise direction about the corresponding pin joint 56. The maximum counterclockwise rotation of elliptical element 55 is approximately 90°, until the adjacent rounded end thereof substantially contacts seat 37 (FIG. 3) of retaining member 53 and frame 31 of the MG is horizontally disposed.

Reference is made now to FIGS. 5-8, presenting slightly curved frame 31 according to one embodiment of the present invention in various views, wherein FIG. 5 shows tongue blade 50, characterized by a plurality of buccaly expended wings 120 (e.g., 2) and/or members 80. One retraction element 354 is also disclosed Maxillary teeth abutment members 40, e.g. two, for contacting the upper teeth or upper maxillary alveoli are illustrated in FIGS. 8-11. While the angular orientation of prior art teeth blades are not adjustable, abutment members 40 of the present invention are adapted to rotate about maxillary cross member 33 (See FIG. 3), in order to facilitate engagement, disengagement or readjustment of an abutment member without having to remove the MG of a patient, as has been practiced heretofore.

Each abutment member 40 which is pivotable about maxillary cross member 33 and is laterally displaceable, is defined by a hollow cylindrical wall which subtends an angle of approximately 270° and by substantially straight elongated walls and extending from each end of cylindrical wall and joining at common distal end. Elongated wall extends tangentially from cylindrical wall, and the tangent point is substantially diametrically opposite to rectangular protrusion extending into the interior of the latter. The exterior side of wall is formed with e.g., three mutually parallel lips extending across the width thereof and with concave portions. Each concave portion terminates with a portion of said lips. Distal end coincides with concave portion and lip. The lateral dimension of cylindrical wall, elongated walls and, protrusion, and lips are essentially equal. Leaf spring is possibly connected to the interior of abutment member, such that one end of the leaf spring is connected to the inner wall of discontinuity, at which elongated walls and are joined, and at its other end is connected to the inner face of cylindrical wall.

Distal portions, i.e., end of the member located inside the oral cavity, are adapted to abut a suitable area within the oral cavity, such as the inner face of a tooth and the alveoli, and to pry the jaws to a maximal opening. After the suitable area is selected, the maxillary teeth abutment members 40 are moved buccally or medially to face the selected suitable area. The abutment members 40 are then rotated by applying a suitable moment thereto to engage the selected area.

Maxillary cross member 33 is substantially tubular and is formed with at least two internally recessed grooves 88 defined by two laterally extending walls 89A and 89B having a spacing therebetween substantially equal to the thickness of protrusion 44. Once protrusion 44 is inserted into groove 88, see FIG. 20A for example, abutment member 40 can be laterally displaced, yet cannot be rotated about the maxillary cross member, due to the contact between the laterally extending walls and protrusion. When protrusion is inserted into groove 88, leaf spring is in a relaxed state. If abutment member 40 is desired to be rotated, e.g. to one of the angular dispositions, a sufficient force is applied thereto such that protrusion is dislodged from groove 88. Leaf spring is then tensed, contacting the periphery of maxillary cross member. After the abutment member is rotated in a desired fashion, the protrusion is inserted into the corresponding groove, and the leaf spring returns to its relaxed state. Releasing the abutment member 40 and allowing it to rotate around the cross member will release the entire MG that can be disengaged from the mouth.

FIGS. 8-11 illustrates said MG according another embodiment of the present invention.

Figure 12:
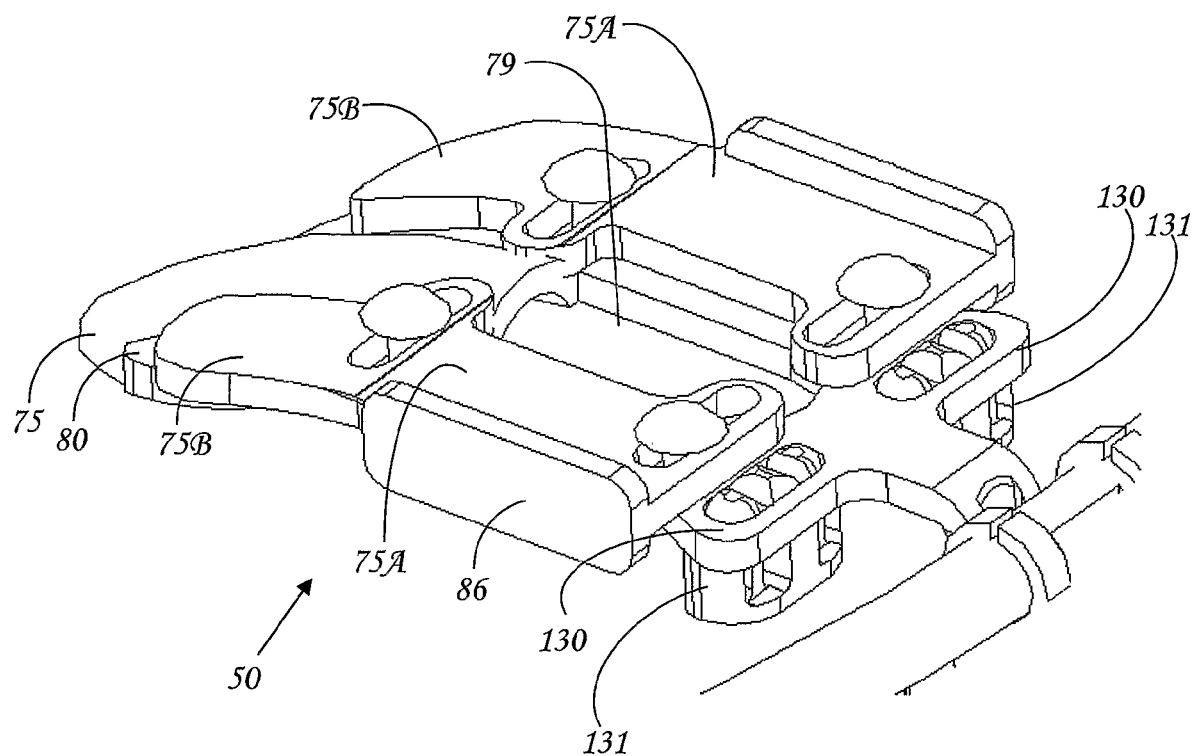
FIGS. 12-14 are perspective close views of the tongue blade and its fast disconnecting means according to another embodiment of the present invention.

FIG. 12 discloses tongue blade 50 according to one embodiment of the present invention, comprises inter alia fixed section 75 which is connected to shaft 52 and perpendicular thereto, and two horizontally displaceable elements 80 ("wings") underlying fixed section 75, by which the width of tongue blade 50 may be adjusted. Wings 80 and their like can be situated between the fixed section 75 and the tongue as shown or can be situated on the other, buccal side of the fixed section 75. Fixed portion 75 is formed with a semi-elliptical opening 79 formed in the middle thereof, with its closed curved end at the outer end thereof, thereby defining a fixed portion with two legs. Fixed section 75 has a planar inner portion 75A, a downwardly curved portion 75B, and a partial tubular portion 75C having its concave side facing downwards. Tubular portion 75C, which protrudes above fixed section 75 and through which an endotracheal tube is insertable and/or interposed between the two legs of downwardly curved portion 75B. Each underlying displaceable element 80 is pivotally connected to the corresponding fixed section 75 by pin 82 and is provided with a wall 86, which facilitates displacement of the corresponding displaceable element 80. In the illustrated example, each displaceable element comprises a curved portion 84 at the outer end thereof which is wider than the main blade portion 85 at the inner end thereof. The inward displacement of displaceable elements 80 is limited upon contact between opposed curved portion 84 of adjacent displaceable elements 80.

It is acknowledged in this respect that member 86 may comprise an elongated ridge directed downwardly, i.e. to the tongue, thus adapted to fix the tongue in a central position in respect to the main longitudinal axis of the tongue blade, preferably wherein the pressed-down tongue pushes wings 120 laterally (buccally). Said ridge us further adapted to prevent the tongue from escaping the tongue-blade upwardly or buccally, providing safer and easier surgery.

Figure 13:
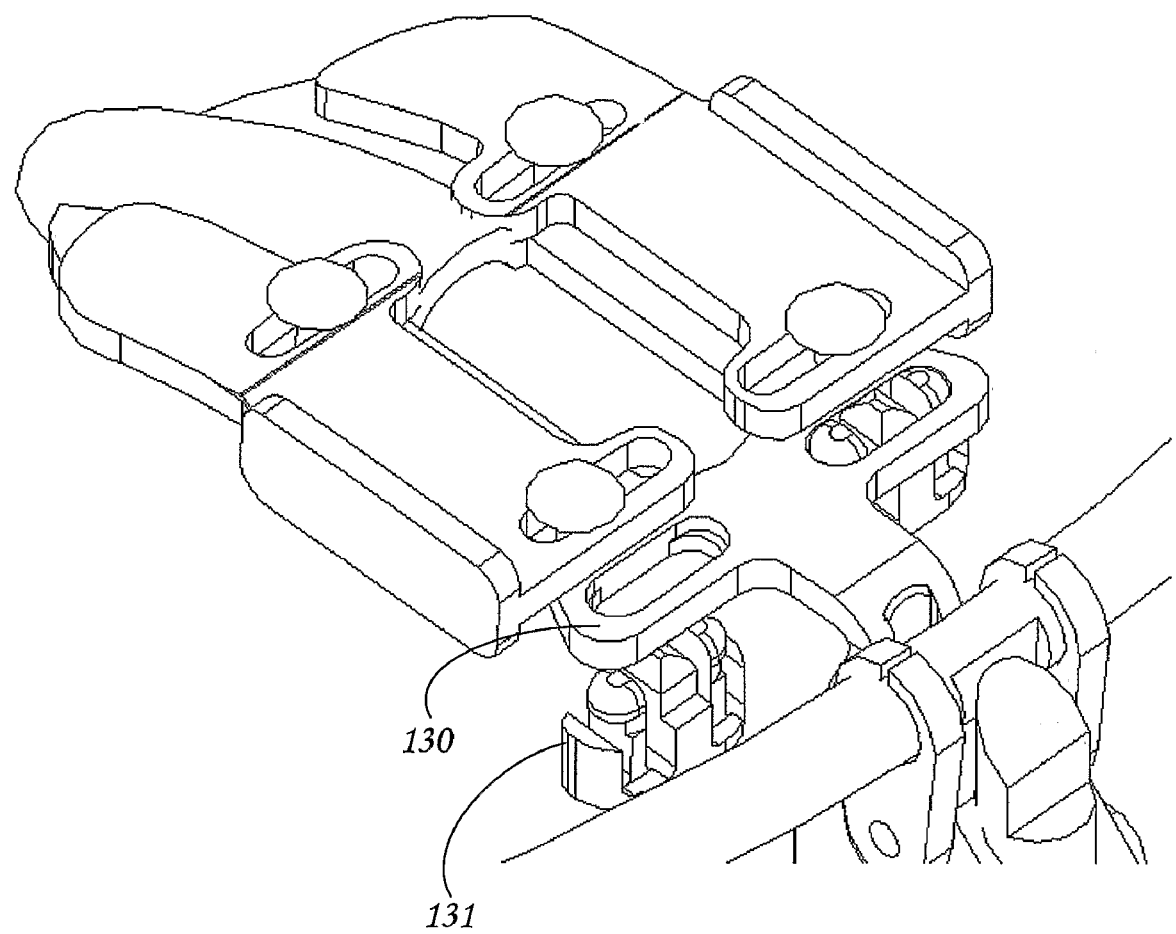
Figure 14:
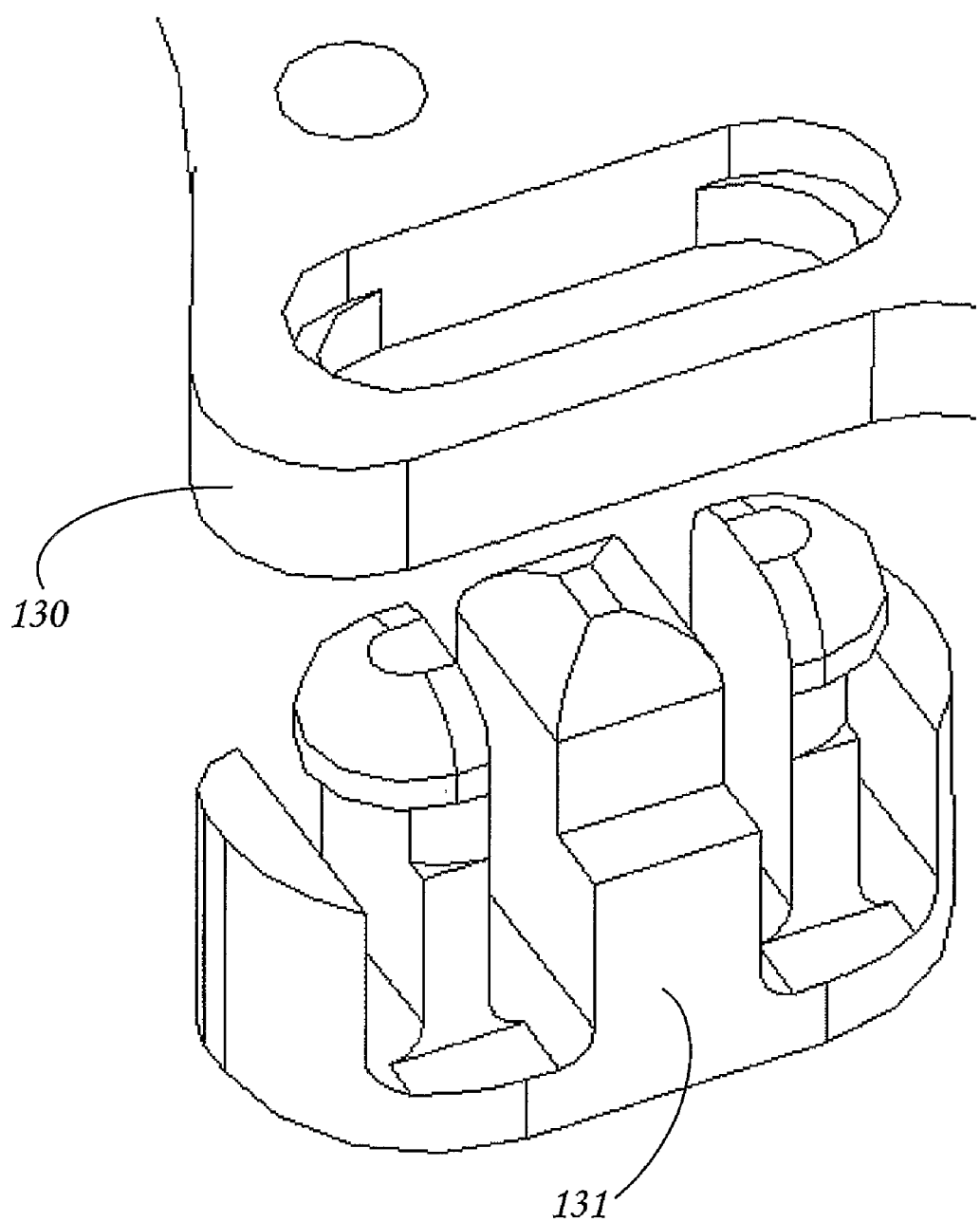

Reference is made now to FIGS. 13-14, presenting a tongue blade fast connecting/disconnecting means according to another embodiment of the present invention. This mechanism further enables a safe operation of the tongue blade, e.g., blade 50, in emergency cases. It comprises in a non limiting manner a plurality e.g., two female 130 sockets and a plurality e.g., two male plugs.

In contrast with prior art mouth gags which employ an external light source, light source may be advantageously directed to any desired region of the oral cavity, and particularly to dark, inaccessible regions, without casting a shadow.

Figure 15:
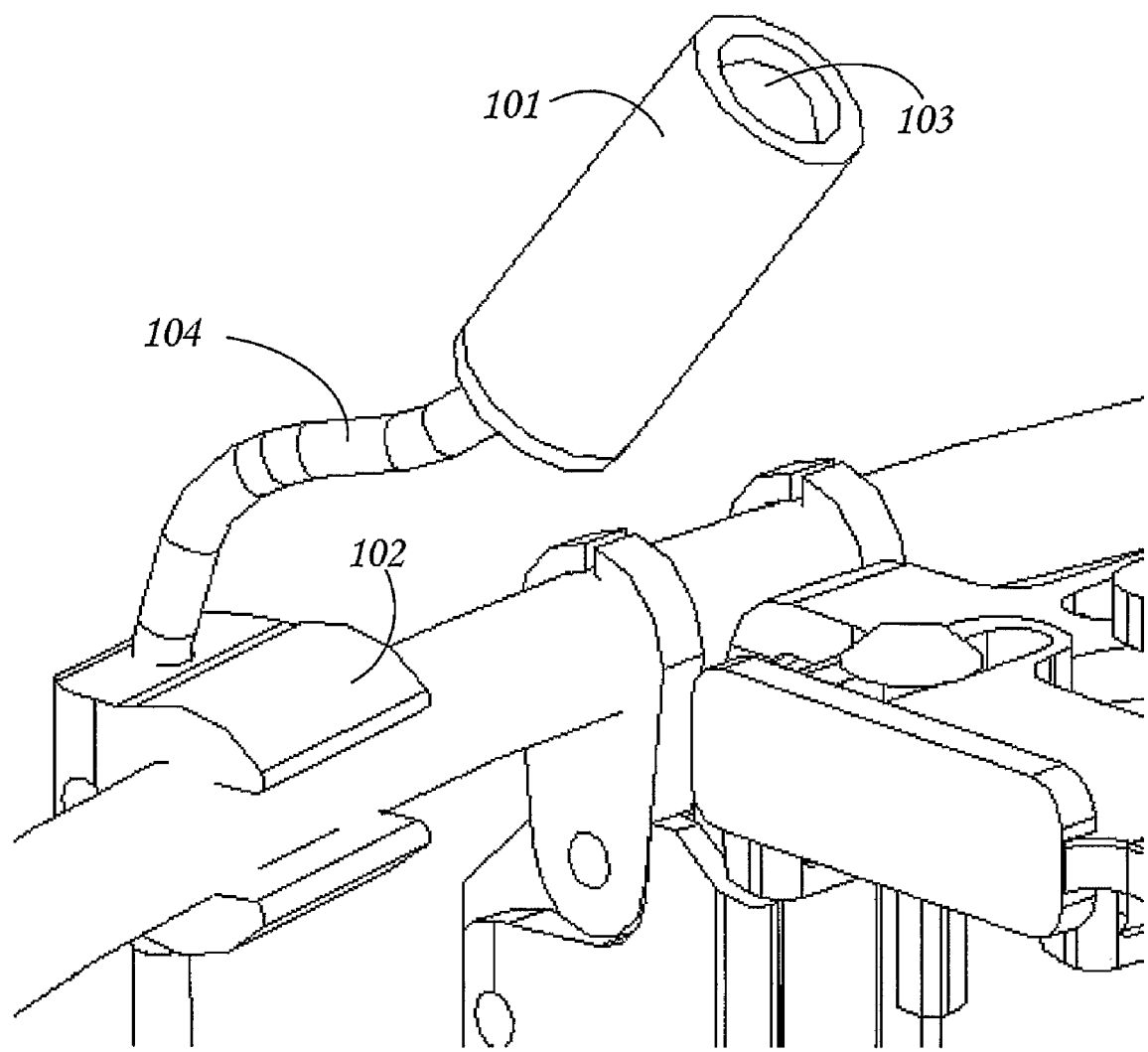
FIGS. 15-16 are perspective close views of the light system according to another embodiment of the present invention.
Figure 16:
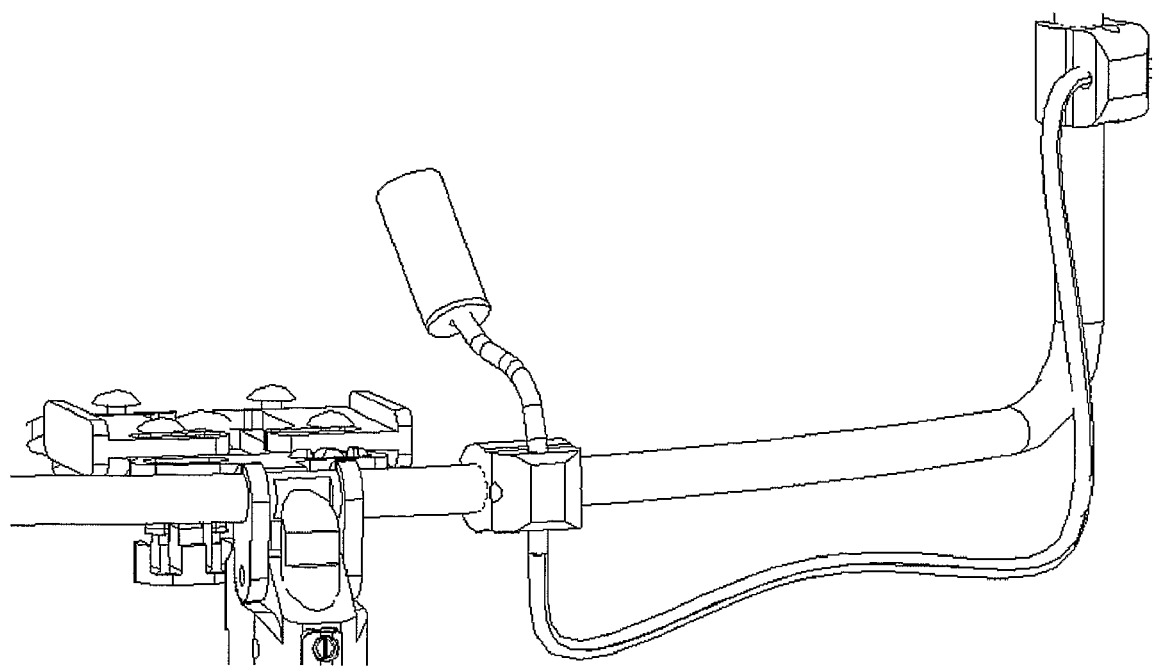

The illumination provided by light source may be generated by any conventional means, such as a lamp, a combination of one or more optical fibers, each of which is used for guiding light or laser directional waves or a LED. The light source is generally powered by conventional means such as by a battery or alternating current. It is acknowledged in this respect that the surgical mouth gag according to this invention may further comprise a plurality of light sources, e.g., 1 to 4 light sources, which are releasably attachable to the frame and directable to any desired region of the oral cavity without casting a shadow. Reference is made hence to FIGS. 15-16 presenting a light system according to one embodiment of the present invention. This system is containing at least one light source 101, which may include lump 103, cables 104 and connectors 102 adapted to reversibly immobilized the same.

Figures 17A, 17B, 17C:
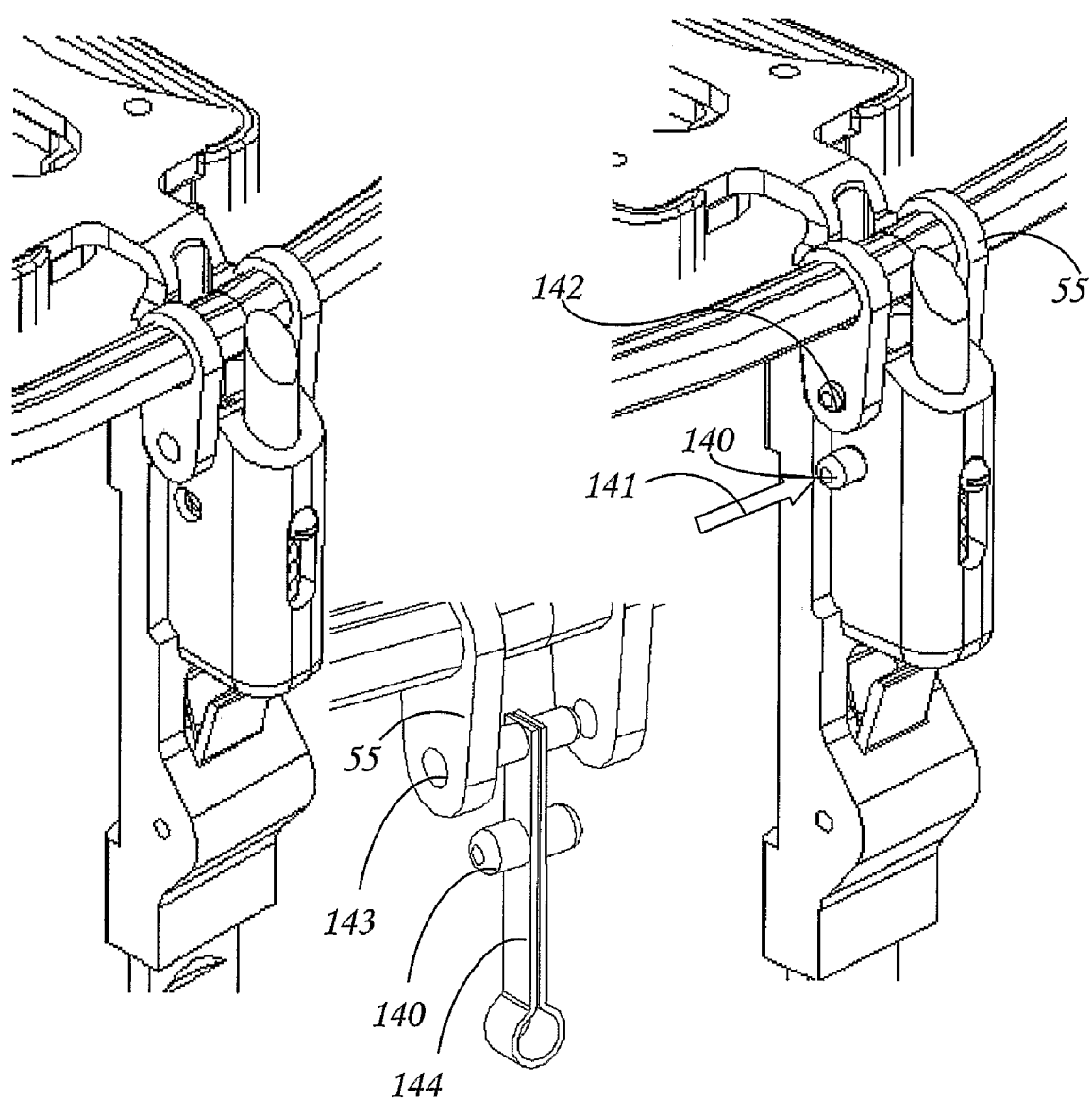
FIGS. 17A-17C and FIG. 18 are perspective close views of the a retaining member and its fast disconnecting means according to another embodiment of the present invention.
Figure 18:
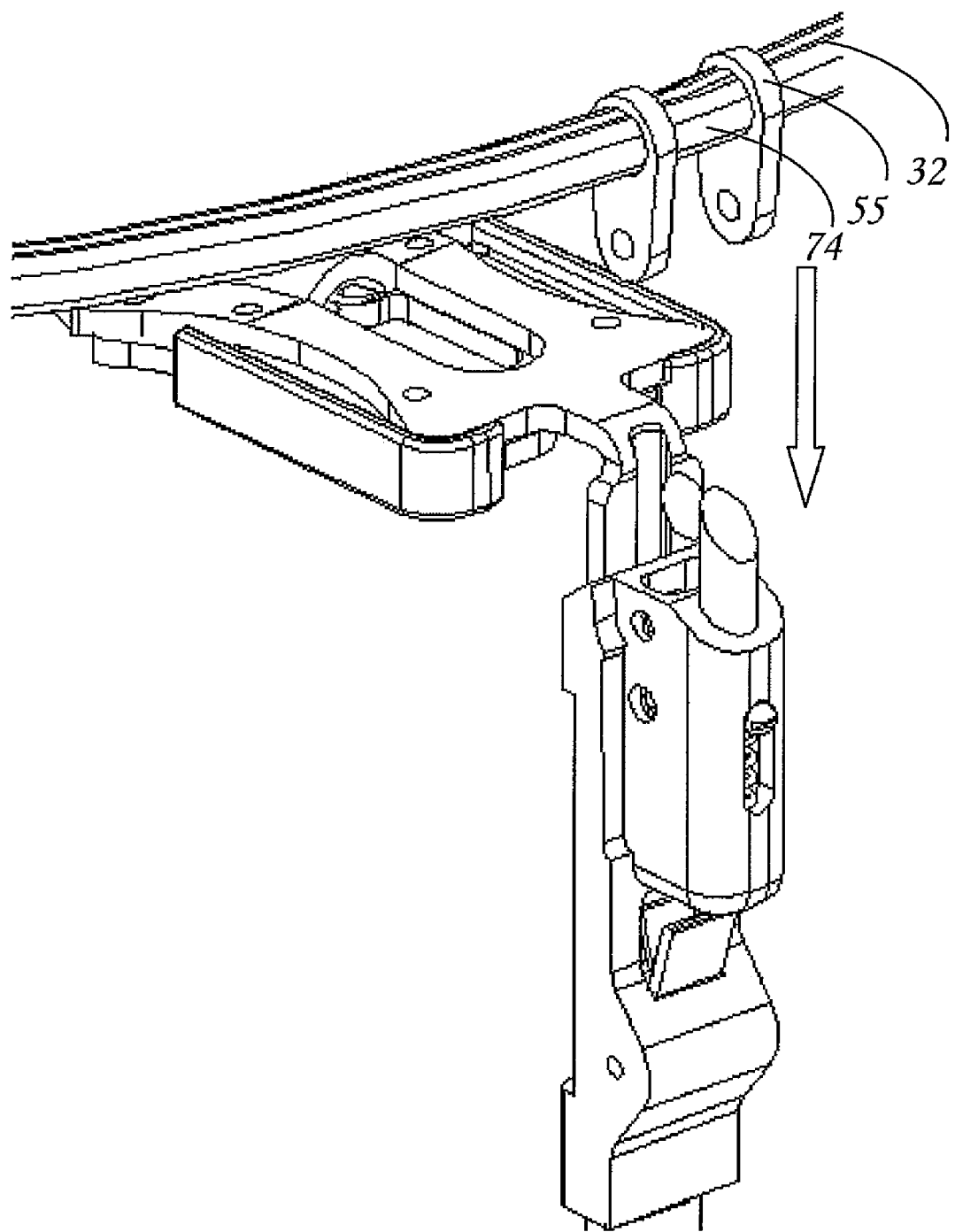
Figure 19A:
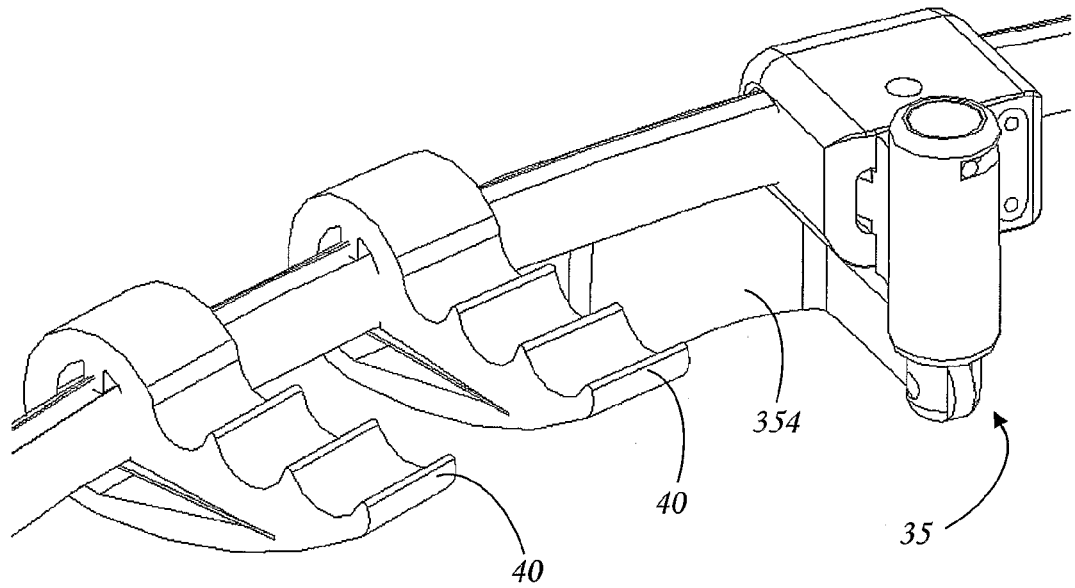
FIGS. 19A-19B are perspective views of the retraction elements and abutment members according to another embodiment of the present invention; and, FIGS. 20A-20B, 21A-21B and 22A-22D are perspective views of the retraction elements and their maneuvering mechanism according to another embodiment of the present invention.
Figure 19B:
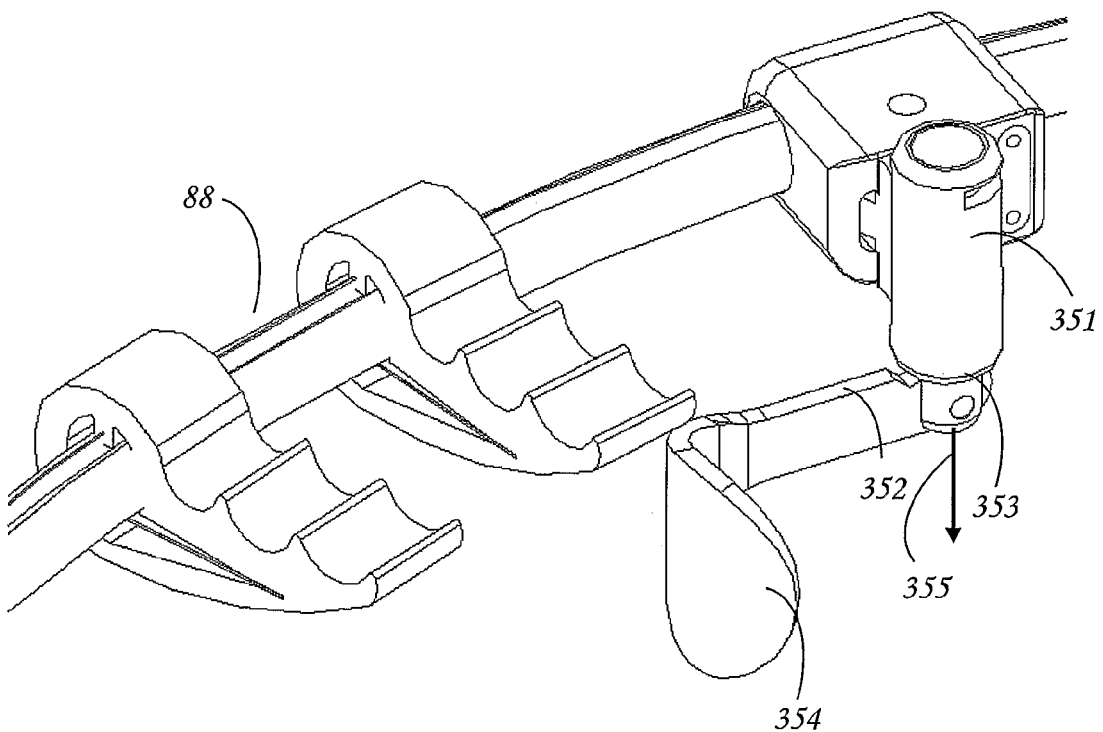

Reference is made now to FIGS. 17A-C presenting a fast disconnecting mechanism for the tongue blade according to yet another embodiment of the present invention. This mechanism comprises in a non-limiting manner a U-shaped spring 144 or the like; a plurality, e.g., two push buttons 140 interconnected to the same in a face-to-face orientation; and a plurality, e.g., two pins 142 also interconnected to said spring in a face-to-face orientation. Said pins are adapted by means of shape and size to be freely and reversibly accommodated in apertures 143 in member 55, such as by pushing or clamping each or both push buttons 140 in a direction 141, a safe disconnection of the blade, and therefore its evacuation from the patient's oral cavity is obtained in case of emergency need. FIG. 18 present the same, wherein tongue blade is disconnected from frame 32, namely from members 55.

FIGS. 19-22 illustrate a rotatable and laterally displaceable retraction element assembly 35 for urging the cheeks away from the oral cavity. Reference is made now to FIG. 19A and 19B, presenting two maxillary teeth abutment members 40 and a single (right) retraction element 35 assembly. Said retraction element 35 is presented in FIG. 19A in one of its folded configurations and in its one of the semi-open configurations in FIG. 19B. Retraction element 35 assembly comprising inter alia, according to this specific embodiment, a shaft housing 351, shaft axis 353, retraction element's handle 352 and retraction element's effecter 354. In a non-limiting manner, said shaft is adapted to be pulled downwardly i.e., along arrow 351, in parallel to the main longitudinal axis of housing 351.

Figure 20A:
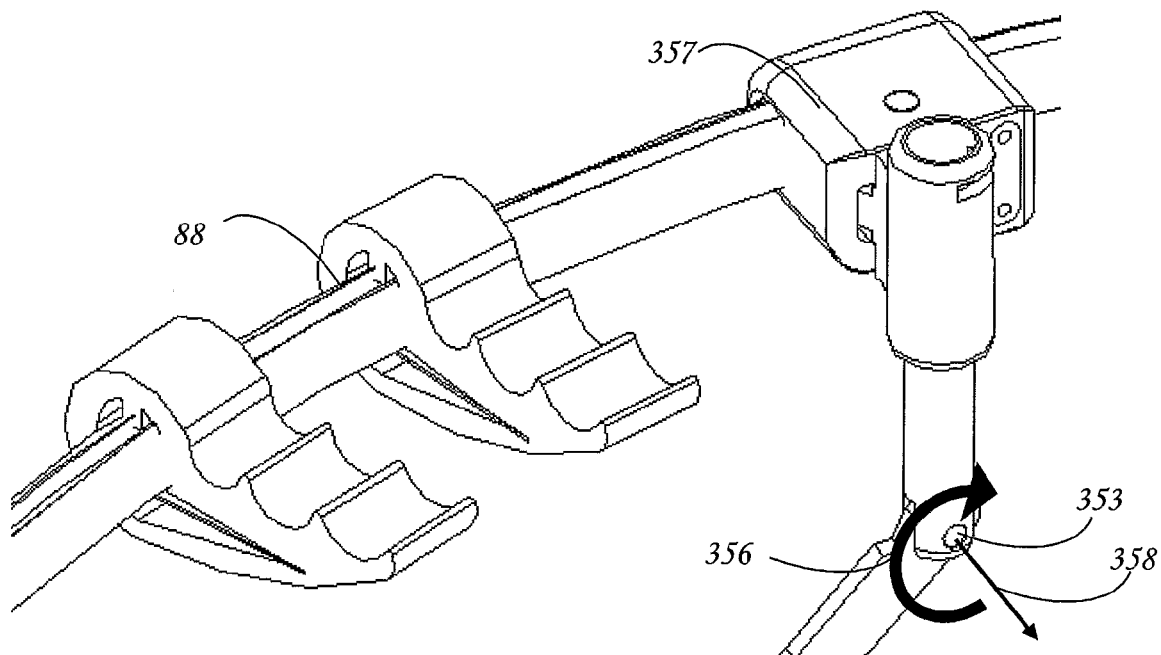
Figure 20B:
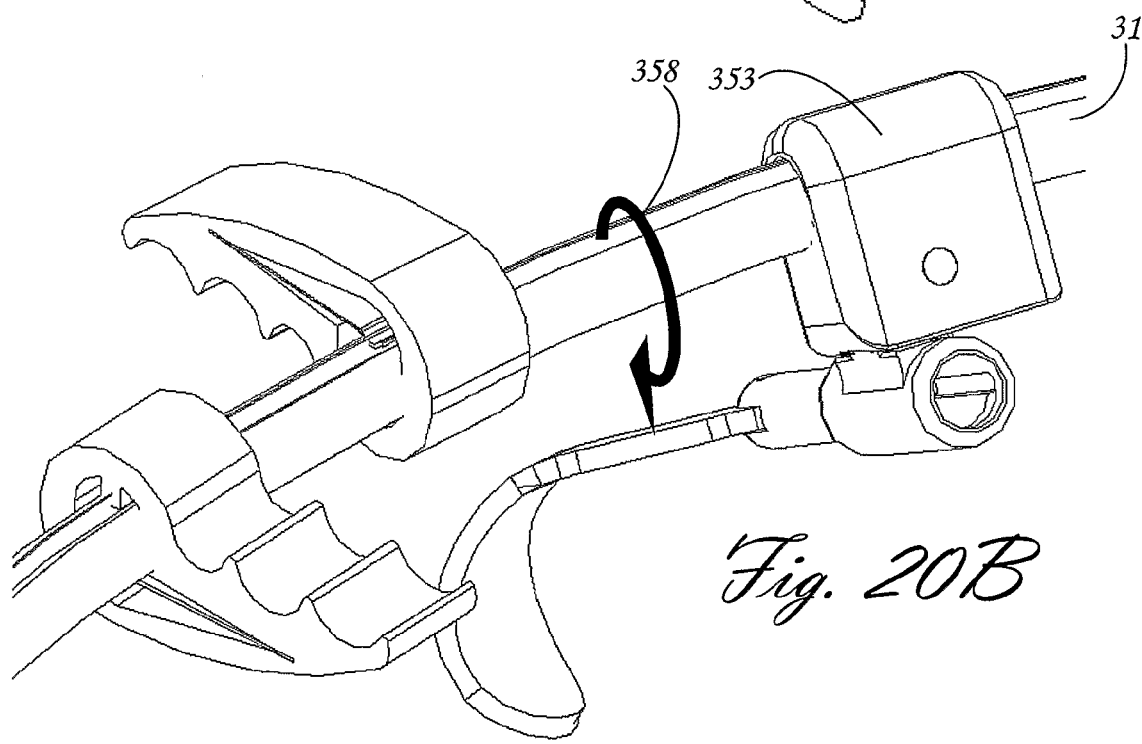

FIGS. 20A and 20B shows the same, wherein the retraction element's handle 352 and retraction element's effecter 354 in its open configuration. Effecter 354 is rotatably (356) mounted in axis 353 by a means of an axle in direction 358. Moreover, adapter 357 is rotatably or maneuverably mounted maxillar frame 31.

Figure 21A:
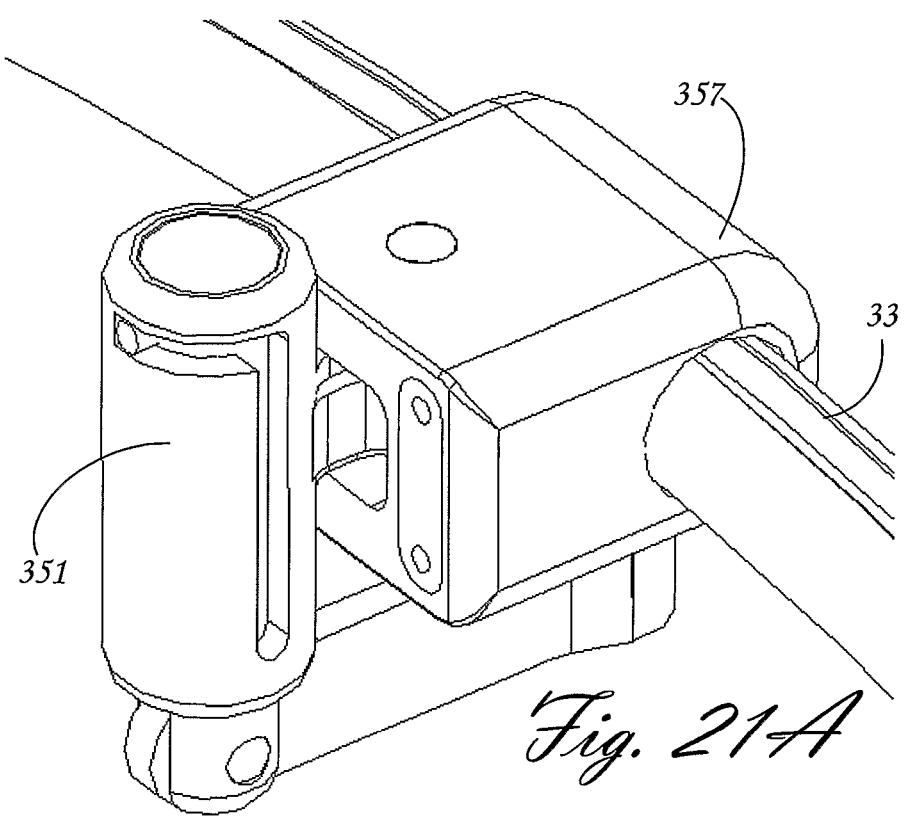
Figure 21B:
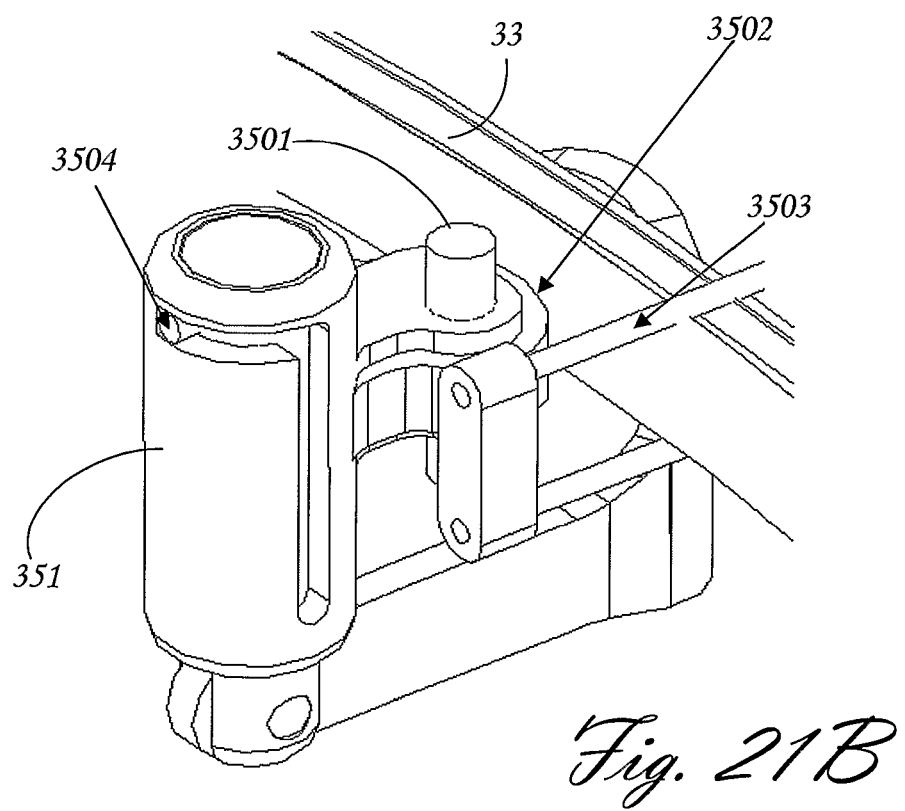

Reference is made now to FIGS. 21A and 21B, schematically presenting adapter 357 locking mechanism. The adapter is in communication with shaft 351 by a means of an accentor 3502 adapted to reversibly lock or attached or forcefully clap frame 31. Pin 3502 is provided as the rotating axle of the same. Anti sliding mechanism 3503 is possibly provided, comprising a plurality of springs and/or flexible rods clapping frame 31. Said mechanism further adapted to position the spring in any predetermined configuration or rotation state. Shaft housing 351 comprising limiting means adapted to avoid adapter's 354 undesired movements at time of the operation. Hence for example, pin 3504 is forced along an L-shaped groove at said housing wall. This mechanism is well adapted to ensure effecter's 354 maneuver before and after operation while a firm and unchangeable configuration is provided at the time of the operation.

Reference is made now to FIGS. 22A-22D, schematically illustrating the locking mechanism, adapted to lock accentor 3502 rotationally (See arrow 3541) to frame 31, and thus the undesired sliding of effecter 354 as a result any force parallel to arrow 3452. FIGS. 22A and 22B presents the released mode of the same, with and without presenting the outer shell of adapter 357, wherein similarly FIG. 22C and 22D presents the locked mode of the same, respectively.

It is in the scope of the invention wherein each of the aforementioned components, namely the retraction elements, abutment members and tongue blade are thus provided with means for emergency release allowing an emergency disengagement of the MG from the patient's mouth.

The tongue blade is released by pressing on button 62 that allows the entire frame to rotate upward from the patient.

The entire retaining member 53 can be released from the maxillary cross member 32 and the main frame by retracting pin joint 56 (its mechanism is not shown).

Each maxillary teeth abutment member 40 is released by pressing on cylindrical wall. Protrusion is released from the maxillary cross member groove 88, thus allowing the abutment member 40 to rotate about mandibular cross member 33 and releasing the entire MG from the patient.

The laterally retracting elements 354 are preferably locked in place by the medial pressure of the distended lips, which exert a moment by means of head portion 140 on the maxillary cross member 33. By pressing on the trigger 96, pin 137 is released and head portion is slightly detached from maxillary cross member 33, thereby releasing the locking position of a retraction element. The arm of a retraction element can be moved medially or rotated upward around the maxillary cross member 33. In the other alternative turning the locking key or pushing the retracting arm sidewise will release it as well.

It is further in the scope of another possible embodiment of the present invention wherein a tube guard is employed, to prevent the bending and obstruction of an endrotracheal tube. This guard transfers the tongue blade pressure onto the lower jaw teeth, rather than onto the ventilation tube, leaving the tube free of any external pressure. A horizontally displaceable tube guard may comprise a U-shaped support, rod being perpendicular to the support, and a knoblike actuator for rotating rod. As actuator is rotated horizontally, the angular disposition of support relative to shaft may be adjusted. Alternatively, the tube guard generally may have an adjustable inclination. Tube guard hence may comprises U-shaped support wherein each of its two legs have a curved connecting portion, rod being perpendicular to the support, plates keyed to support and connected to rod by a geared connection, and a knoblike actuator for rotating rod. As actuator is rotated, the inclination of support relative to fixed portion of the tongue blade changes. Alternatively, a tongue guide having a U-shaped plate may be fixedly attached, e.g. by welding, to fixed portion of the tongue blade by vertical connecting element. Alternatively, a tongue guide in a form of a spacer block made of softer, heat resistant material, e.g., Teflon™ or Delerin™, is attached to the tongue blade fixed member on one or both sides on the contact point with the mandible teeth preventing pressure from the endo-tracheal tube.

A separate thread retaining accessory device made of longitudinal elliptical spring can be clipped onto the cross or longitudinal members at will.

As shown, all angles and protrusion that can catch the suturing threads were rounded and beveled in order to prevent the entanglement of said surgical suturing material.

The MG of the present invention, as described in the foregoing description, considerably reduces the dexterity and skill for the engagement thereof within the oral cavity prior to the commencement of a suitable surgical procedure, such as cleft palate surgery, pharyngeal surgery, tonsillectomy, tumor surgery in the mouth, cheeks and pharynges, and some dental procedures. While the duration of an engaging or removing procedure involving an MG of the prior art requires dexterity, is risky and may take several minutes, an engaging or removing procedure involving an MG of the present invention requires only a few seconds.

In operation, frame 31 of the present invention is angularly separated from fixed portion 75 (see e.g., FIG. 12) of the tongue blade by approximately 90 degrees. Retraction elements 354 are upwardly rotated about maxillary cross member 33 such that arm is positioned vertically above carrier and abutment members 40 are oriented such that distal end thereof is vertically above cylindrical wall. While fixed section 75 of the tongue blade is at its uppermost position, the tongue blade is inserted into the oral cavity by a procedure similar to the insertion of a laryngoscope. As the tongue blade is pressing on the tongue, the endo-tracheal tube is placed in the depression or introduced through semielliptical opening of the tongue blade. If the width of tongue blade is significantly different than the mandibular floor, i.e. the distance between the alveoli, displaceable elements "wings" 80 and or 120 are adjusted accordingly to conform to the mandible width, covering the tongue entirely. Once the tongue blade is positioned onto the tongue and lowered to retract the tongue and mandible, the entire MG is rotated 90 degrees until elliptical elements 55 are locked by the corresponding seat of retaining member and the frame assumes its functional position during a surgical procedure, whereby side rods are vertically disposed. Thereinafter, maxillary teeth abutment members 40 are brought medially, sliding on the cross member to their desired position and rotated against the maxillary teeth or alveoli. Retraction elements 354 are brought medially, sliding on the cross member then rotated into the mouth and buccally pushed until the cheeks and the lateral lip commissures are tight, thus locking arm against maxillary cross member 33. The endo-tracheal tube guard and light source are adjusted, and the surgeon may then carry out the desired surgical procedure. When it is desired to remove the MG from the oral cavity, the effortless release of the retraction elements 354 and/or abutment members 40 disengages the entire MG.

Especial attention has been directed in this invention to eliminating all proprusions, sharp angles and avoiding exposed crevices that may entangle the surgical threads. All activation buttons are rounded and protected from entanglements. The interface between moving parts on the main frame and the frame members, as well as parts themselves are beveled in such a way to prevent threads catching and wedging, which is a common problem in commercially existing MGs.

Hence, for example, members 62 and 64 are characterized by a rounded and smooth contours and contain no protruding edges, such as screw heads or nail-tips. Moreover, members 357 and 40 are characterized by a ring-like shape, i.e. comprise a fully-closed clipping means.

According to yet another embodiment of the present invention, the said device and parts thereof are at least partially made of bio-compatible materials. For example, ventilating tube protector 131 is made of flexible plastic components.

While some embodiments of the invention have been described by way of illustration, it will be apparent that the invention can be carried into practice with many modifications, variations and adaptations, and with the use of numerous equivalents or alternative solutions that are within the scope of persons skilled in the art, without departing from the spirit of the invention or exceeding the scope of the claims.

The invention claimed is:

1. A safe surgical mouth gag (MG) comprising a substantially planar frame larger than the maximal mouth aperture which is defined by at least two cross members, being a longitudinal maxillary cross member and a mandibular cross member and by at least one rod connecting said maxillary and said mandibular cross members; and modules maneuverably interconnected to the same, said modules are selected from:
   a. a tongue blade having an elongated shaft approximately perpendicular to said frames' plane, which is vertically displaceable with respect to said mandibular cross member;
   b. a retaining member within which said tongue blade shaft is slidably displaceable, adapted for reversibly retaining said tongue blade at a predetermined vertical distance with respect to said mandibular cross member; said mandibular cross member and the entire frame is rotatable with respect to said retaining member;
   c. retraction elements for urging the cheeks away from the oral cavity; the said are pivotally maneuverable about said maxillary cross member and are laterally displaceable;
   d. abutment members for contacting the upper teeth or upper maxilla, pivotally maneuverable about said maxillary cross member and are laterally displaceable; and,
   e. at least one light auxiliary located adjacent to oral cavity, adapted to illuminate the same effectively;
   such as a prompt removal of the MG from the oral cavity is ensured, also in an emergency removal procedures, individually set and adjusted for each patient and the existing devices and their parts are difficult or in some cases impossible to manipulate;
   wherein the retaining member comprises an inwardly facing track within which the tongue blade shaft is slidably displacement; an outwardly facing concave seat for receiving each corresponding elliptical element; a locking assembly for preventing the rotation of the maxillary cross member; and means for setting the vertical distance between the tongue blade and the mandibular cross member.

2. The surgical mouth gag according to claim 1, wherein the track has two opposed vertically extending buccal faces which are formed with upper and lower stepped portions at the inner edge thereof, guide elements laterally extending from the inner edge of said upper and lower stepped portions defining the track within which the shaft is slidable.

3. The surgical mouth gag according claim 2, wherein the locking assembly is provided with a button having a pointed upper portion and a helical spring which biases the button upwardly.

4. The surgical mouth gag as claimed in claim 1, wherein the tongue blade comprises a fixed section connected to the shaft and essentially perpendicular thereto, and two horizontally displaceable elements underlying or overlying said fixed section, by which the width of the tongue blade is adjustable.

5. The surgical mouth gag as claimed in claim 4, wherein the tongue blade is provided with an opening through which an endotracheal tube is insertable.

6. The surgical mouth gag as claimed in claim 1, wherein the button, angles protrusions and setting means are curvilinear.

7. The surgical mouth gag as claimed in claim 1, wherein the retaining member is detachable from the maxillary cross member.

8. The surgical mouth gag as claimed in claim 1, wherein the retraction element comprises a carrier which is laterally displaceable along, and rotatable about, the maxillary cross member; an arm pivotally connected to said carrier by means of a pin fixedly mounted onto opposed side faces of said carrier; a release trigger for said arm; and a U-shaped retractor blade connected to said arm such that a curved portion of said blade is lingually oriented.

9. The surgical mouth gag as claimed in claim 8, wherein the arm has a curvilinear head portion configured such that the rotation of the retraction element about the maxillary cross member is prevented when said head portion is in pressing engagement with the maxillary cross member.

10. The surgical mouth gag as claimed in claim 8, wherein the retraction element is provided with means for preventing the lateral displacement thereof.

11. The surgical mouth gag as claimed in claim 1, wherein each abutment member is laterally displaceable along, and rotatable about, the maxillary cross member.

12. The surgical mouth gag as claimed in claim 11, wherein the abutment member comprises a hollow partial cylindrical wall; substantially straight elongated walls extending from each end of said cylindrical wall and joining at a common distal end; a protrusion extending into the interior of said cylindrical wall for engaging a similarly shaped laterally extending groove formed in the maxillary cross member; and a plurality of mutually parallel lips formed in the exterior of one of said elongated walls for abutting a suitable area within the oral cavity and for subsequently prying the jaws to a maximal opening.

13. The surgical mouth gag as claimed in claim 11, wherein the abutment member is rotatable about the maxillary cross member upon disengagement of the protrusion from the similarly shaped groove.

14. The surgical mouth gag as claimed in claim 1, further comprising a light source which is releasably attachable to the frame and directable to any desired region of the oral cavity without casting a shadow.

15. The surgical mouth gag as claimed in claim 1, further comprising a guard for an endo-tracheal tube.

16. The surgical mouth gag as claimed in claim 15, wherein the tube guard is U-shaped.

17. The surgical mouth gag as claimed in claim 15, wherein the tube guard is connected to the fixed section of the tongue blade.

18. The surgical mouth gag as claimed in claim 15, wherein the tube guard is horizontally displaceable.

19. The surgical mouth gag as claimed in claim 15, wherein the inclination of the tube guard is adjustable.

20. The surgical mouth gag as claimed in claim 15, wherein the tube guard is in the form of one or two spacer-blocks between the tongue blade and the teeth.

21. The surgical mouth gag as claimed in claim 1, characterized by smooth, continuous surfaces, such that all protrusions, shaft angles and exposed crevices are eliminated, further wherein said surgical mouth gag is quickly collapsible.

22. A safe surgical mouth gag (MG) comprising a substantially planar frame larger than the maximal mouth aperture which is defined by at least two cross members, being a longitudinal maxillary cross member and a mandibular cross member, and by at least one rod connecting said maxillary and said mandibular cross members; and modules maneuverably interconnected to the same, said modules are selected from:
   a. a tongue blade having an elongated shaft approximately perpendicular to said frames' plane, which is vertically displaceable with respect to said mandibular cross member;
   b. a retaining member within which said tongue blade shaft is slidably displaceable, adapted for reversibly retaining said tongue blade at a predetermined vertical distance with respect to said mandibular cross member; said mandibular cross member and the entire frame is rotatable with respect to said retaining member;

c. retraction elements for urging the cheeks away from the oral cavity; the said are pivotally maneuverable about said maxillary cross member and are laterally displaceable;

d. abutment members for contacting the upper teeth or upper maxilla, pivotally maneuverable about said maxillary cross member and are laterally displaceable; and, e. at least one light auxiliary located adjacent to oral cavity, adapted to illuminate the same effectively;

such as a prompt removal of the MG from the oral cavity is ensured, also in an emergency removal procedures, individually set and adjusted for each patient and the existing devices and their parts are difficult or in some cases impossible to manipulate, wherein the retaining element is adapted to rotate 90 degree around the maxillary cross member and further adapted to be locked into either positions.

23. A safe surgical mouth gag (MG) comprising a substantially planar frame larger than the maximal mouth aperture which is defined by at least two cross members, being a longitudinal maxillary cross member and a mandibular cross member and by at least one rod connecting said maxillary and said mandibular cross members; and modules maneuverably interconnected to the same, said modules are selected from:

a. a tongue blade having an elongated shaft approximately perpendicular to said frames' plane, which is vertically displaceable with respect to said mandibular cross member;

b. a retaining member within which said tongue blade shaft is slidably displaceable adapted for reversibly retaining said tongue blade at a predetermined vertical distance with respect to said mandibular cross member; said mandibular cross member and the entire frame is rotatable with respect to said retaining member;

c. retraction elements for urging the cheeks away from the oral cavity; the said are pivotally maneuverable about said maxillary cross member and are laterally displaceable;

d. abutment members for contacting the upper teeth or upper maxilla, pivotally maneuverable about said maxillary cross member and are laterally displaceable; and, e. at least one light auxiliary located adjacent to oral cavity, adapted to illuminate the same effectively;

such as a prompt removal of the MG from the oral cavity is ensured, also in an emergency removal procedures, individually set and adjusted for each patient and the existing devices and their parts are difficult or in some cases impossible to manipulate, wherein the mandibular cross member is provided with two equally sized planar elements which are recessed at diametrically opposite ends thereof, a pointed upper portion of a locking assembly button being in a pressing relation with one of said planar elements when the button is raised.

24. A safe surgical mouth gag (MG) comprising a substantially planar frame larger than the maximal mouth aperture which is defined by at least two cross members, being a longitudinal maxillary cross member and a mandibular cross member and by at least one rod connecting said maxillary and said mandibular cross members; and modules maneuverably interconnected to the same, said modules are selected from:

a. a tongue blade having an elongated shaft approximately perpendicular to said frames' plane, which is vertically displaceable with respect to said mandibular cross member;

b. a retaining member within which said tongue blade shaft is slidably displaceable, adapted for reversibly retaining said tongue blade at a predetermined vertical distance with respect to said mandibular cross member; said mandibular cross member and the entire frame is rotatable with respect to said retaining member;

c. retraction elements for urging the cheeks away from the oral cavity; the said are pivotally maneuverable about said maxillary cross member and are laterally displaceable;

d. abutment members for contacting the upper teeth or upper maxilla, pivotally maneuverable about said maxillary cross member and are laterally displaceable; and, e. at least one light auxiliary located adjacent to oral cavity, adapted to illuminate the same effectively;

such as a prompt removal of the MG from the oral cavity is ensured, also in an emergency removal procedures, individually set and adjusted for each patient and the existing devices and their parts are difficult or in some cases impossible to manipulate, wherein the maxillary cross member is prevented from rotating in one rotational direction due to a force applied by a pointed upper portion of a locking assembly button onto a corresponding planar element and is prevented from rotating in other rotational direction due to a reactive force applied by a seat onto a corresponding elliptical element.

\* \* \* \* \*